US008101570B2

(12) United States Patent
Takahashi et al.

(10) Patent No.: US 8,101,570 B2
(45) Date of Patent: Jan. 24, 2012

(54) SINGLE BRANCH HEPARIN-BINDING GROWTH FACTOR ANALOGS

(75) Inventors: Kazuyuki Takahashi, Germantown, MD (US); Paul O. Zamora, Gaithersburg, MD (US); Louis A. Pena, Poquott, NY (US); Xinhua Lin, Plainview, NY (US)

(73) Assignee: BioSurface Engineering Technologies, Inc., Rockville, MD (US)

( * ) Notice: Subject to any disclaimer, the term of this patent is extended or adjusted under 35 U.S.C. 154(b) by 0 days.

(21) Appl. No.: 12/786,256

(22) Filed: May 24, 2010

(65) Prior Publication Data

US 2010/0298218 A1 Nov. 25, 2010

Related U.S. Application Data

(63) Continuation of application No. 11/359,173, filed on Feb. 21, 2006, now abandoned.

(60) Provisional application No. 60/655,570, filed on Feb. 22, 2005.

(51) Int. Cl.
*A61K 38/16* (2006.01)

(52) U.S. Cl. ....... 514/7.6; 514/21.3; 514/21.4; 530/323; 530/324; 530/325; 530/399

(58) Field of Classification Search ................. None
See application file for complete search history.

(56) References Cited

U.S. PATENT DOCUMENTS

| | | | |
|---|---|---|---|
| 3,272,204 A | 9/1966 | Artandi et al. |
| 4,172,128 A | 10/1979 | Thiele et al. |
| 4,193,138 A | 3/1980 | Okita |
| 4,563,350 A | 1/1986 | Nathan et al. |
| 4,747,848 A | 5/1988 | Maini |
| 4,842,575 A | 6/1989 | Hoffman, Jr. et al. |
| 5,108,436 A | 4/1992 | Chu et al. |
| 5,197,977 A | 3/1993 | Hoffman, Jr. et al. |
| 5,202,311 A | 4/1993 | Folkman et al. |
| 5,326,695 A | 7/1994 | Andersson et al. |
| 5,509,899 A | 4/1996 | Fan et al. |
| 5,510,418 A | 4/1996 | Rhee et al. |
| 5,512,545 A | 4/1996 | Brown et al. |
| 5,563,046 A | 10/1996 | Mascarenhas et al. |
| 5,608,035 A | 3/1997 | Yanofsky et al. |
| 5,635,597 A | 6/1997 | Barrett et al. |
| 5,643,873 A | 7/1997 | Barrett et al. |
| 5,648,458 A | 7/1997 | Cwirla et al. |
| 5,650,234 A | 7/1997 | Dolence et al. |
| 5,654,276 A | 8/1997 | Barrett et al. |
| 5,665,114 A | 9/1997 | Weadock et al. |
| 5,668,110 A | 9/1997 | Barrett et al. |
| 5,674,977 A | 10/1997 | Gariepy |
| 5,679,637 A | 10/1997 | Lappi et al. |
| 5,679,673 A | 10/1997 | Bowen et al. |
| 5,684,136 A | 11/1997 | Godowski |
| 5,728,802 A | 3/1998 | Barrett et al. |
| 5,759,515 A | 6/1998 | Rhodes et al. |
| 5,767,234 A | 6/1998 | Yanofsky et al. |
| 5,770,704 A | 6/1998 | Godowski |
| 5,773,569 A | 6/1998 | Wrighton et al. |
| 5,786,322 A | 7/1998 | Barrett et al. |
| 5,786,331 A | 7/1998 | Barrett et al. |
| 5,789,182 A | 8/1998 | Yayon et al. |
| 5,830,851 A | 11/1998 | Wrighton et al. |
| 5,830,995 A | 11/1998 | Shoyab et al. |
| 5,854,207 A | 12/1998 | Lee et al. |
| 5,861,476 A | 1/1999 | Barrett et al. |
| 5,866,113 A | 2/1999 | Hendriks et al. |
| 5,869,451 A | 2/1999 | Dower et al. |
| 5,880,096 A | 3/1999 | Barrett et al. |
| 5,902,799 A | 5/1999 | Herrmann et al. |
| 5,916,585 A | 6/1999 | Cook et al. |
| 5,932,462 A | 8/1999 | Harris et al. |
| 5,945,457 A | 8/1999 | Plate et al. |
| 5,952,474 A | 9/1999 | Kayman et al. |
| 5,955,588 A | 9/1999 | Tsang et al. |
| 5,965,532 A | 10/1999 | Bachovchin |
| 5,989,866 A | 11/1999 | Deisher et al. |
| 5,994,104 A | 11/1999 | Anderson et al. |
| 6,001,364 A | 12/1999 | Rose et al. |
| 6,011,002 A | 1/2000 | Pastan et al. |
| 6,030,812 A | 2/2000 | Bauer et al. |
| 6,051,648 A | 4/2000 | Rhee et al. |

(Continued)

FOREIGN PATENT DOCUMENTS

WO     WO00/18921     4/2000

(Continued)

OTHER PUBLICATIONS

Ahmed, Asif et al., "Role of VEFGF Receptor-1 (Flt-1) in Mediating Calcium-Dependent Nitric Oxide Release and Limiting DNA Synthesis in Human Trophoblast Cells", *Lab Invet*, vol. 76(6) 1997 , 779-791.

Andrades, Jose A. et al., "A Recombinant Human TGF-B1 Fusion Protein with Collagen-Binding Domain Promostes Migration, Growth, and Differentiation of Bone Marrow Mesenchymal Cells", *Experimental Cell Research* vol. 250 1999 , 485-498.

Baird, Andrew et al., "Receptor- and heparin-binding domains of basic fibroblast growth factor", *Proc. Natl. Acad. Sci.*, vol. 85 Apr. 1988 , 2324-2328.

Ballinger, Marcus D. et al., "Semirational design of a potent, artificial agonist of fibroblast growth factor receptors", *Nature Biotechnology* vol. 17 1999 , 1199-1204.

(Continued)

*Primary Examiner* — Anish Gupta
(74) *Attorney, Agent, or Firm* — Janeen Vilven; Peacock Myers, P.C.

(57) ABSTRACT

A heparin-binding growth factor (HBGF) analog having two substantially similar sequences (homodimeric sequences) branched from a single amino acid residue, where the sequences are analogs of a particular HBGF that binds to a heparin-binding growth factor receptor (HBGFR), or alternatively that bind to a HBGFR without being an analog of any particular HBGF. The homodimeric sequences may be derived from any portion of a HBGF. The synthetic HBGF analog may be an analog of a hormone, a cytokine, a lymphokine, a chemokine or an interleukin, and may bind to any HBGFR. Further provided are preparations for medical devices, pharmaceutical compositions and methods of using the same.

11 Claims, 9 Drawing Sheets

U.S. PATENT DOCUMENTS

| | | | |
|---|---|---|---|
| 6,096,798 | A | 8/2000 | Luthra et al. |
| 6,099,562 | A | 8/2000 | Ding et al. |
| 6,120,904 | A | 9/2000 | Hostettler et al. |
| 6,121,236 | A | 9/2000 | Ben-Sasson |
| 6,168,784 | B1 | 1/2001 | Offord et al. |
| 6,174,530 | B1 | 1/2001 | Rose et al. |
| 6,174,721 | B1 | 1/2001 | Innis |
| 6,214,795 | B1 | 4/2001 | Benjamin et al. |
| 6,217,873 | B1 | 4/2001 | Rose et al. |
| 6,231,600 | B1 | 5/2001 | Zhong |
| 6,231,892 | B1 | 5/2001 | Hubbell et al. |
| 6,235,716 | B1 | 5/2001 | Ben-Sasson |
| 6,248,057 | B1 | 6/2001 | Mavity et al. |
| 6,251,864 | B1 | 6/2001 | Dower et al. |
| 6,258,371 | B1 | 7/2001 | Koulik et al. |
| 6,270,788 | B1 | 8/2001 | Koulik et al. |
| 6,284,503 | B1 | 9/2001 | Caldwell et al. |
| 6,294,359 | B1 | 9/2001 | Fiddes et al. |
| 6,306,165 | B1 | 10/2001 | Patnaik et al. |
| 6,309,660 | B1 | 10/2001 | Hsu et al. |
| 6,323,323 | B1 | 11/2001 | Sledziewski et al. |
| 6,326,468 | B1 | 12/2001 | Canne et al. |
| 6,342,591 | B1 | 1/2002 | Zamora et al. |
| 6,350,731 | B1 | 2/2002 | Jehanli et al. |
| 6,368,347 | B1 | 4/2002 | Maini et al. |
| 6,377,349 | B1 | 4/2002 | Fercher |
| 6,387,978 | B2 | 5/2002 | Ronan et al. |
| 6,406,687 | B1 | 6/2002 | Luthra et al. |
| 6,410,044 | B1 | 6/2002 | Chudzik et al. |
| 6,426,332 | B1 | 7/2002 | Rueger et al. |
| 6,451,543 | B1 | 9/2002 | Kochendoerfer et al. |
| 6,458,889 | B1 | 10/2002 | Trollsas et al. |
| 6,491,965 | B1 | 12/2002 | Berry et al. |
| 6,497,729 | B1 | 12/2002 | Moussy et al. |
| 6,514,534 | B1 | 2/2003 | Sawhney |
| 6,534,591 | B2 | 3/2003 | Rhee et al. |
| 6,548,634 | B1 | 4/2003 | Ballinger et al. |
| 6,585,765 | B1 | 7/2003 | Hossainy et al. |
| 6,596,699 | B2 | 7/2003 | Zamora et al. |
| 6,630,580 | B2 | 10/2003 | Tsang et al. |
| 6,818,018 | B1 | 11/2004 | Sawhney |
| 6,846,853 | B2 | 1/2005 | Shimp |
| 6,863,899 | B2 | 3/2005 | Koblish et al. |
| 6,921,811 | B2 | 7/2005 | Zamora et al. |
| 6,949,251 | B2 | 9/2005 | Dalal et al. |
| 6,984,393 | B2 | 1/2006 | Amsden |
| 7,025,990 | B2 | 4/2006 | Sawhney |
| 7,041,641 | B2 | 5/2006 | Rueger et al. |
| 7,166,574 | B2 | 1/2007 | Pena et al. |
| 7,241,736 | B2 | 7/2007 | Hunter et al. |
| 7,414,028 | B1 | 8/2008 | Zamora et al. |
| 7,468,210 | B1 | 12/2008 | Zamora |
| 7,482,427 | B2 | 1/2009 | Pena et al. |
| 7,528,105 | B1 | 5/2009 | Pena et al. |
| 7,598,224 | B2 | 10/2009 | Zamora et al. |
| 7,671,012 | B2 | 3/2010 | Zamora et al. |
| 7,700,563 | B2 | 4/2010 | Pena et al. |
| 2001/0014662 | A1 | 8/2001 | Rueger et al. |
| 2002/0115836 | A1 | 8/2002 | Tsang et al. |
| 2002/0160098 | A1 | 10/2002 | Zamora et al. |
| 2003/0224996 | A1 | 12/2003 | Opperman et al. |
| 2004/0038348 | A1 | 2/2004 | Pena et al. |
| 2004/0068266 | A1 | 4/2004 | Delmotte |
| 2004/0087505 | A1 | 5/2004 | Pena et al. |
| 2004/0151764 | A1 | 8/2004 | Zamora |
| 2005/0196425 | A1 | 9/2005 | Zamora |
| 2005/0222394 | A1 | 10/2005 | Zamora et al. |
| 2006/0024347 | A1 | 2/2006 | Zamora et al. |
| 2006/0199764 | A1 | 9/2006 | Zamora et al. |
| 2006/0205652 | A1 | 9/2006 | Zamora et al. |
| 2008/0063622 | A1 | 3/2008 | Zamora et al. |
| 2008/0160169 | A1 | 7/2008 | Zamora et al. |
| 2008/0166392 | A1 | 7/2008 | Zamora et al. |
| 2008/0227696 | A1 | 9/2008 | Takahashi et al. |
| 2009/0111743 | A1 | 4/2009 | Takahashi |
| 2009/0143566 | A1 | 6/2009 | Zamora et al. |
| 2010/0267650 | A1 | 10/2010 | Zamora et al. |

FOREIGN PATENT DOCUMENTS

| | | |
|---|---|---|
| WO | WO0064481 | 11/2000 |
| WO | WO02/04015 | 1/2002 |
| WO | WO0210221 | 2/2002 |
| WO | WO02/20033 | 3/2002 |
| WO | WO0219963 | 3/2002 |
| WO | WO-02/062823 | 8/2002 |

OTHER PUBLICATIONS

Binetruy-Tournaire, Roselyne et al., "Identification of a Peptide Blocking Vascular Endothelial Growth Factor (VEGF)-mediated Angiogenesis", *The EMBO Journal*, vol. 19, No. 7 2000, 1525-1533.

Bork, Peer, "Go Hunting in Sequence Databases But Watch Out for Traps", *TIG* Vo. 12 No. 10 Oct. 1996, 425-427.

Bork, Peer, "Powers and Pitfalls in Sequence Analysis: the 70% Hurdle", *Genome Research* vol. 10 2000, 398-400.

Brennand, David M. et al., "Identification of a Cyclic Peptide Inhibitor of Platelet-Derived Growth Factor-BB Receptor-Binding and Mitogen-Induced DNA Synthesis in Human Fibroblasts", *FEBS Letters*, 413 1997, 70-74.

Brenner, Steve, "Errors in Genome Annotation", *Trends in Genetics* vol. 15 No. 4 Apr. 1999, 132-133.

Carmeliet, Peter et al., "Growing Better Blood Vessels", *Nature Biotechnology* vol. 19 2001, 1019-1020.

Dawson, Philip E. et al., "Synthesis of Native Proteins by Chemical Ligation", *Annu. Rev. Biochem*, 2000, 69 2000, 923-960.

Dikov, Michael M. et al., "A Functional Fibroblast Growth Factor-1 Immunoglogulin Fusion Protein", *The Journal of Biological Chemistry*, vol. 273, No. 25 Jun. 19, 1998, 15811-15817.

Doerks, Tobias, "Protein annotation: detective work for function prediction", *Trends in Genetics* vol. 14 No. 6 Jun. 1998, 248-250.

Engstrom, Ulla et al., "Identification of a Peptide Antagonist for Platelet-Derived Growth Factor", *The Journal of Biological Chemistry*, vol. 273, No. 25 1998, 16581-16587.

EOM, Khee D. et al., "Tandem Ligation of Multipartite Peptides with Cell-Permeable Activity", *J. Am. Chem. Soc.* vol. 125 2003, 73-83.

Feeley, Brian et al., "Influence of BMP's on the Formation of Osteoblastic Lesions in Metastatic Prostate Cancer", *Journal of Bone and Mineral Research*, vol. 20 No. 12 2005, 2189-2199.

Gay, Cyril G. et al., "Interleukin 1 regulated heparin-binding growth factor 2 gene expression in vascular smooth muscle cells", *Proc. Natl. Acad. Sci. USA*, vol. 88 Jan. 1991, 296-300.

Hasan, Maemunah et al., "IL-12 is a Heparin-Binding Cytokine", *The Journal of Immunology* vol. 162 1999, 1064-1070.

Healy, Kevin et al., "Designing biomaterials to direct biological responses", Ann N Y Acad Sci. 875 1999, 24-35.

Hoke, David E. et al., "A Heparin Binding Synthetic Peptide from Human HIP/RPL29 Fails to Specifically Differentiate Between Anticoagulantly Active and Inactive Species of Heparin", *Journal of Negative Results in BioMedicine* vol. 2. No. 1 2003, 1-10.

Kirsch, Thomas et al., "BMP-2 Antagonists Emerge from Alterations in the Low-Affinity Binding Epitope for Receptor BMPR-II", *EMBO Journal*, vol. 19, No. 13 2000, 3314-3324.

Kloen, P. et al., "BMP signaling components are expressed in human fracture callus", *Bone* 33 2003, 362-371.

Kochendoerfer, Gerd G. et al., "Design and Chemical Synthesis of Homogeneous Polymer-Modified Erythropoiesis Protein", *Science*, vol. 299 2003, 884-887.

Konishi, Sadahiko et al., "Hydroxyapatite Granule Graft Combined with Recombinant Human bone Morphogenic Protein-2 for Solid Lumbar Fusion", *Journal of Spinal Disorders & Techniques*, vol. 15, No. 3 2002, 237-244.

Laredo, James et al., "Silyl-heparin bonding improves the patency and in vivo thromboresistance of carbon-coated polytetrafluoroethylene vascular grafts", *The Midwestern Vascular Surgical Society* Sep. 2003, 1-7.

Lin, Xinhua et al., "A Synthetic, Bioactive PDGF Mimetic with Binding to Both α-PDGF and β-PDGF Receptors", *Growth Factors* vol. 25 No. 2 2007, 87-93.

Lu, Xinjie et al., "Preferential antagonism of the interactions of the integrin alpha IIb beta 3 with immobilized glycoprotein ligans by snake-venom RGD (Arg-Gly-Asp) proteins", *Biochem J* 304 1994, 929-936.

Minamide, Akihito et al., "Evaluation of Carriers of Bone Morphogenetic Protein for Spinal Fusion", *Spine* vol. 26, No. 8 2001, 933-939.

Murnaghan, Mark et al., "Time for treating bone fracture using rhBMP-2: A randomised placebo controlled mouse fracture trial", *Journal of Orthopaedic Research* 23 2005, 625-631.

Ngo, Thomas et al., "Computational Complexity; Protein Structure Prediction, and the Levinthal Paradox", *The Protein Foling Problem and Terminary Structure Prediction*, Chapter 14 1994, 491-495.

Niikura, T. et al., "Gloval Gene Profiling in Experimental Fracture Nonunions Reveals a Down Regulation of BMP Gene Expression", *52nd Annual Meeting of the Orthopaedic Research Society*, Paper No. 1673 2006.

Ostman, Arne et al., "Identification of Three Amino Acids in the Platelet-Derived Growth Factor (PDGF) B-chain that are Important for Binding to the PDGF B-Receptor", *The Journal of Biological Chemistry*, vol. 266, No. 16, Issue of Jun. 5, 1991, 10073-10077.

Paris, Francois et al., "Endothelial Apoptosis as the Primary Lesion Initiating Intestinal Radiation Damage in Mice", *Science* vol. 293 2001, 293-297.

Pellegrini, Luca, "Role of Heparan sulfate in fibroblast growth factor signalling: a structural view", *Current Opinion in Structural Biology* 2001, 629-634.

Ray, Jasohara et al., "A 10-amino acid sequence of fibroblast growth factor 2 is sufficient for its mitogenic activity on neural progenitor cells", *Proc. Natl. Acad. Sci.* USA vol. 94 1997, 7047-7052.

Richardson, Thomas P. et al., "Polymeric system for dual growth factor delivery", *Nature Biotechnology* vol. 19 2001, 293-297.

Rusnati, Marco et al., "avB3 Integrin Mediates the Cell-adhesive Capacity and Biological Activity of Basic Fibroblast Growth Factor (FGF-2) in Cultured Endothelial Cells", *Molecular Biology of the Cell* vol. 8 1997, 2449-2461.

Saito, Atsuhiro et al., "Activation of osteo-progenitor cells by a novel synthetic peptide derived from the bone morphogenetic protein-2 knuckle epitope", *Biochimica et Biophysica Acta* 1651 2003, 60-67.

Saito, Atsuhiro et al., "Prolonged ectopic calcification induced by BMP-2-derived synthetic peptide", *Journal of Biomedical Materials Research Part A*, vol. 70 No. 1 2004, 115-121.

Seol, Yang-Jo et al., "Enhanced osteogenic promotion around dental implants with synthetic binding motif mimicking bone morphogenetic protein (BMP)-2", *Journal of Biomedical Materials Research Part A*, vol. 77 No. 3 2006, 599-607.

Shen, Wei-Chiang et al., "Poly(l-lysine) has different membrane transport and drug-carrier properties when complexed with heparin", *Proc Natl Acad Sci* USA vol. 78, No. 12 Dec. 1981, 7589-93.

Skolnick, Jeffrey et al., "From genes to protein structure and function: novel applications of computational approaches in the genomic era", *TIBTECH* vol. 18 Jan. 2000, 34-39.

Smith, Temple F. et al., "The challenges of genome sequence annotation of "The devil is in the details"", *Nature Biotechnology*, vol. 15 Nov. 1997, 1222-1223.

Sood, R. et al., "MDS1/EVI1 enhances TGF-B1 signaling and strengthens its growth-inhibitory effect, but the leukemia-associated fusion protein AML1/MDS1/EVI1, product of the t(3:21), abrogates growth-inhibition in response to TGF-B1", *Leukemia* vol. 13 1999, 348-357.

Takizawa, Takuma et al., "Directly Linked Soluble IL-6 Receptor-IL-6 Fusion Protein Induces Astrocyte Differentiation from Neuroepithelial Cells Via Activation of STAT3", *Cytokine* vol. 13 2001, 272-279.

Tanaka, H. et al., "Involvement of bone morphogenic protein-2 (BMP-2) in the pathological ossification process of the spinal ligament", *Rheumatology* 2001;40 May 9, 2001, 1163-1168.

Tong, Yen et al., "Peptide surface modification of poly(tetrafluoroethylene-co-hexafluoropropylene) enhances its interaction with central nervous system nuerons", *J Biomed Mater Res* 42 1998, 85-95.

Tung, Ching-Hsuan et al., "Novel branching membrane translocational peptide as gene delivery vector", *Bioorg Med Chem* 10(11) 2002, 3609-3614.

Varkey, Mathew et al., "Growth factor delivery for bone tissue repair: an update", *Expert Opin. Drug Deliver.* (2004) 1(1) 2004, 19-34.

Verrecchio, Angela, "Design of Peptides with High Affinities for Heparin and Endothelial Cell Proteoglycans", *The Journal of Biological Chemistry*, vol. 275, No. 11 Mar. 17, 2000, 7701-7707.

Wells, James A., "Additivity of Mutational Effects in Proteins", *American Chemical Society*, vol. 29, No. 37 Sep. 18, 1990, 8509-8516.

Yano, Akira et al., "RGD motif enhances immunogenicity and adjuvanicity of peptide antigens following intranasal immunization", *Vaccine* 22(2) 2003, 237-243.

Yoneda, Atsuko, "Engineering of an FGF-proteoglycan fusion protein with heparin-independent, mitogenic activity", *Nature Biotechnology* vol. 18 Jun. 2000, 641-644.

Zamora, Paul O. et al., "Local Delivery of Basic Fibroblast Growth Factor (bFGF) Using Adsorbed Silyl-heparin, Benzyl-bis(dimethylsilylmethyl)oxycarbamoyl-heparin", *Bioconjugate Chem.* 2002 Aug. 20, 2002, 920-926.

Hsu, Hailing et al., "Tumor Necrosis Factor Receptor Family Member RANK Mediates Osteoclast Differentiation and Activation Induced by Osteoprotegerin Ligand", *Proc. Natl. Acad. Sci.* vol. 96 1999, 3540-3545.

Fenstermaker, Robert A. et al., "A Cationic Region of the Platelet-Derived Growth Factor (PDGF) A-Chain (Arg159-Lys160-Lys161) is Required for Receptor Binding and Mitogenic Activity of the PDGF-AA Homodimer", *J. Biol. Chem.*, vol. 268 No. 14 1993, 10482-10489.

Iida, Shinya et al., "Human hst-2 (FGF-6) Oncogene: cDNA Cloning and Characterization", *Oncogene* vol. 7 No. 2, 1992, 303-309.

Marics, Irene et al., "Characterization of the HST-Related FGF-6 Gene, a New Member of the Fibroblast Factor Gene Family", *Oncogene* vol. 4 No. 3, 1989, 335-340.

Merrifield, Bruce, "Concept and Early Development of Solid-Phase Peptide Synthesis", Methods in Enzymol, vol. 289, 1997, 3-13.

Nakatake, Yuhki et al., "Identification of a Novel Fibroblast Growth Factor, FGF-22, Preferentially Expressed in the Inner Root Sheath of the Hair Follicle", Biochim. Biophys. Acta. vol. 1517 No. 3, 2001, 460-463.

Nishimura, Tetsuya et al., "dentification of a Novel FGF, FGF-21, Preferentially Expressed in the Liver", Biochim. Biophys. Acta. vol. 1492 No. 1, 2000, 203-206.

Sidhu, Sachdev, "Phage Display for Selection of Novel Binding Peptides", Methods Enzymol, vol. 328, 2000, 333-363.

Wade, John D. et al., "Solid Phase Peptide Synthesis; Recent Advances and Applications", Austral. Biotechnol., vol. 3 No. 6, 1993, 332-336.

Aaronson, Stuart A. et al., "Human KGF is FGF-related with Properties of a Paracrine Effector of Epithelial Cell Growth", Science vol. 245 No. 4919, 1989, 752-755.

Aaronson, Stuart A. et al., "Keratinocyte Growth Factor. A Fibroblast Growth Factor Family Member with Unusual Target Cell Specificity", Annals NY Acad. Sci. vol. 638, 1991, 62-77.

Abraham, Judith A. et al., "Heparin-Binding EGF-like Growth Factor: Characterization of Rat and Mouse cDNA Clones, Protein Domain Conservation Across Species, and Transcript Expression in Tissues", Biochem. Biophys. Res. Commun. vol. 190 Issue 1, 1993, 125-133.

Bates, Brian et al., "Biosynthesis of Human Fibroblast Growth Factor 5", Mol. Cell Biol., vol. 11 No. 4, 1991, 1840-1845.

Blunt, Allison G. et al., "Overlapping Expression and Redundant Activation of Mesenchymal Fibroblast Growth Factor (FGF) Receptors by Alternatively Spliced FGF-8 Ligands", J. Biol. Chem. vol. 272 No. 6, 1997, 3733-3738.

Burgess, Wilson H. et al., "The Heparin-Binding (Fibroblast) Growth Factor Family of Proteins", Ann. Rev. Biochem. vol. 58, 1989, 575-606.

Burt, David W., "Evolutionary Grouping of the Transforming Growth Factor-Beta Superfamily", Biochem. Biophys. Res. Commun. vol. 184 Issue 2, 1992, 590-595.

Courty, Jose et al., "Mitogenic Properties of a New Endothelial Cell Growth Factor Related to Pleiotrophin", Biochem. Biophys. Res. Commun. vol. 180 Issue 1, 1991, 145-151.

Dubrulle, Julien et al., "FGF Signaling Controls Somite Boundary Position and Regulates Segmentation Clock Control of Spatiotemporal Hox Gene Activation", Cell vol. 106 Issue 2, 2001, 219-232.

Fekete, Donna, "Ear rings: FGF3 involvement comes full circle", Trends in Neurosci., vol. 23 No. 8, 2000, 332.

Fox, John E., "Multiple Peptide Synthesis", Mol. Biotechnol., vol. 3 No. 3, 1995, 249-258.

Gemel, Joanna, "Structure and Sequence of Human FGF8", Genomics vol. 35 Issue 1, 1996, 253-257.

Greene, J. M. et al., "Identification and Characterization of a Novel Member of the Fibroblast Growth Factor Family", Eur J. Neurosci vol. 10, No. 5, 1998, 1911-1925.

Hampton, Brian S. et al., "Structural and Functional Characterization of full-length Heparin-Binding Growth Associated Molecule", Mol. Biol. Cell. vol. 3 Issue 1, 1992, 85-93.

Higashiyama, Shigeki et al., "A Heparin-Binding Growth Factor Secreted by Macrophage Like Cells that is Related to EGF", Science vol. 251 No. 4996, 1991, 936-939.

Hoshikawa, Masamitsu et al., "Structure and Expression of a Novel Fibroblast Growth Factor, FGF-17, Preferentially Expressed in the Embryonic Brain", Biochem. Biophys. Res. Commun. vol. 244 No. 1, 1998, 187-191.

Hu, Mickey C. et al., "FGF-18, a Novel Member of the Fibroblast Growth Factor Family, Stimulates Hepatic and Intestinal Proliferation", Mol. Cell Biol. vol. 18 No. 10, 1998, 6063-6074.

Huber, Daniel et al., "Amino-Terminal Sequences of a Novel HeparinBinding Protein with Mitogenic Activity for Endothelial Cells from Human Bovine, Rat, and Chick Brain: High Interspecies Homology", Neurochem. Res. vol. 15, 1990, 435-439.

Jeffers, Michael et al., "Identification of a Novel Human Fibroblast Growth Factor and Characterization of its Role in Oncogenesis", Cancer Res. vol. 61, No. 7, 2001, 3131-3138.

Kok, L. D. S. et al., "Cloning and Characterization of a cDNA Encoding a Novel Fibroblast Growth Factor Preferentially Expressed in Human Heart", Biochem. Biophys. Res. Comm. vol. 255 No. 3, 1999, 717-721.

Kuo, Ming-Der, "Characterization of Heparin-Binding Growth-Associated Factor Receptor in NIH 3T3 Cells", Biochem. Biophys. Res. Commun. vol. 182 Issue 1, 1992, 188-194.

Lin, Xinhua et al., "Augmentation of Osseous Phenotypes In Vivo with a Synthetic Peptide", Journal of Orthopaedic Research, 2007, 531-539.

Lin, Xinhua, "Multidomain Synthetic Peptide B2A2 Synergistically Enhances BMP-2 In Vitro", Journal of Bone and Mineral Research vol. 20, No. 4, 2005, 693-703.

Lin, Xinhua et al., "Synthetic Peptide F2A4-K-NS Mimics Fibroblast Growth Factor-2 in Vitro and is Angiogenic In Vivo", International Journal of Molecular Medicine vol. 17, No. 5, 2006, 833-839.

Marchese, C. et al., "Human Keratinocyte Growth Factor Activity on Proliferation and Differentiation of Human Keratinocytes: Differentiation Reponse Distinguishes KGF from EGF Family", J. Cellular Physiol. vol. 144 Issue 2, 1990, 326-332.

Marikovsky, Moshe et al., "Appearance of Heparin-Binding EGF-like Growth Factor in Wound Fluid as a Response to Injury", Proc. Natl. Acad. Sci. (USA) vol. 90 No. 9, 1993, 3889-3893.

McWhirter, John R. et al., "A Novel Fibroblast Growth Factor Gene Expressed in the Developing Nervous System is a Downstream Target of the Chimeric Homeodomain Oncoprotein E2A-Pbx1", Development vol. 124 No. 17, 1997, 3221-3232.

Miyake, Ayumi et al., "Structure and Expression of a Novel Member, FGF-16, of the Fibroblast Growth Factor Family", Biochem. Biophys. Res. Commun. vol. 243 No. 1, 1998, 148-152.

Miyamoto, Masaaki et al., "Molecular Cloning of a Novel Cytokine cDNA Encoding the Ninth Member of the Fibroblast Growth Factor Family, Which has a Unique Secretion Pattern", Mol. Cell. Biol. vol. 13 No. 7, 1993, 4251-4259.

Naruo, Ken-Ichi et al., "Novel Secretory Heparin-Binding Factors from Human Glioma Cells (Glia-Activating Factors) Involved in Glial Cell Growth", J. Biol. Chem. vol. 268 No. 4, 1993, 2857-2864.

Nyfeler, Rolf, "Peptide Synthesis via Fragment Condensation", Methods Mol. Biol., vol. 35, 1994, 303-316.

Ohbayashi, Norihiko et al., "Structure and Expression of the mRNA Encoding a Novel Fibroblast Growth Factor, FGF-18", J. Biol. Chem. vol. 273 No. 29, 1998, 18161-18164.

Ohmachi, Shigeki et al., "FGF-20, a Novel Neurotrophic Factor, Preferentially Expressed in the Substantia Nigra Pars Compacta of Rat Brain", Biochem. Biophys. Res. Commun. vol. 277 No. 2, 2000, 355-360.

Sakamoto, Hiromi et al., "Adenovirus-mediated transfer of the HST-1 (FGF4) gene induces increased levels of platelet count in vivo", Proc. Natl. Acad. Sci. USA, vol. 91 No. 26, 1994, 12368-12372.

Shimada, Takahashi et al., "Cloning and Characterization of FGF23 as a Causative Factor of Tumor-Induced Osteomalacia", Proc. Natl. Acad. Sci. (USA) vol. 98 No. 11, 2001, 6500-6505.

Tanaka, Shinji et al., "A Novel Isoform of Human Fibroblast Growth Factor 8 is Induced by Androgens and Associated with Progression of Esophageal Carcinoma", Dig. Dis. Sci. vol. 46 No. 5, 2001, 1016-1021.

Xie, Ming-Hong et al., "FGF-19, a Novel Fibroblast Growth Factor with Unique Specificity for FGFR4", Cytokine vol. 11 No. 10, 1999, 729-735.

Xu, Jingsong et al., "Genomic Structure, Mapping, Activity and Expression of Fibroblast Growth Factor 17", Mechanisms of Development vol. 83, 1999, 165-178.

Yamashita, Tetsuo et al., "Identification of a Novel Fibroblast Growth Factor, FGF-23, Preferentially Expressed in the Ventrolateral Thalamic Nucleus of the Brain", Biochem. Biophys. Res. Commun. vol. 277 No. 2, 2000, 494-498.

Zhan, Xi et al., "The Human FGF-5 Oncogene Encodes a Novel Protein Related to Fibroblast Growth Factors", Mol. Cell Biol. vol. 8 No. 8, 1988, 3487-3495.

SEQUENCE LISTING

```
<160> NUMBER OF SEQ ID NOS: 107

<210> SEQ ID NO 1
<211> LENGTH: 6
<212> TYPE: PRT
<213> ORGANISM: Artificial
<220> FEATURE:
<223> OTHER INFORMATION: Heparin binding motif
<220> FEATURE:
<221> NAME/KEY: misc_feature
<222> LOCATION: (1)..(3)
<223> OTHER INFORMATION: Lys or Arg
<220> FEATURE:
<221> NAME/KEY: misc_feature
<222> LOCATION: (4)..(5)
<223> OTHER INFORMATION: any naturally or non-naturally occuring amino
      acid
<220> FEATURE:
<221> NAME/KEY: misc_feature
<222> LOCATION: (6)..(6)
<223> OTHER INFORMATION: Lys or Arg

<400> SEQUENCE: 1

Xaa Xaa Xaa Xaa Xaa Xaa
1               5

<210> SEQ ID NO 2
<211> LENGTH: 10
<212> TYPE: PRT
<213> ORGANISM: Artificial
<220> FEATURE:
<223> OTHER INFORMATION: Heparin binding motif

<400> SEQUENCE: 2

Arg Lys Arg Lys Leu Glu Arg Ile Ala Arg
1               5                   10

<210> SEQ ID NO 3
<211> LENGTH: 10
<212> TYPE: PRT
<213> ORGANISM: Artificial
<220> FEATURE:
<223> OTHER INFORMATION: Heparin binding motif

<400> SEQUENCE: 3

Arg Lys Arg Lys Leu Gly Arg Ile Ala Arg
1               5                   10

<210> SEQ ID NO 4
<211> LENGTH: 10
<212> TYPE: PRT
<213> ORGANISM: Artificial
```

-continued

```
<220> FEATURE:
<223> OTHER INFORMATION: Heparin binding motif

<400> SEQUENCE: 4

Arg Lys Arg Lys Leu Trp Arg Ala Arg Ala
1               5                   10

<210> SEQ ID NO 5
<211> LENGTH: 9
<212> TYPE: PRT
<213> ORGANISM: Artificial
<220> FEATURE:
<223> OTHER INFORMATION: Heparin binding motif

<400> SEQUENCE: 5

Arg Lys Arg Leu Asp Arg Ile Ala Arg
1               5

<210> SEQ ID NO 6
<211> LENGTH: 11
<212> TYPE: PRT
<213> ORGANISM: Artificial
<220> FEATURE:
<223> OTHER INFORMATION: Heparin binding motif

<400> SEQUENCE: 6

Arg Lys Arg Lys Leu Glu Arg Ile Ala Arg Cys
1               5                   10

<210> SEQ ID NO 7
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 7

Tyr Arg Ser Arg Lys Tyr Thr Ser Trp Tyr Val Ala Leu Lys Arg
1               5                   10                  15

<210> SEQ ID NO 8
<211> LENGTH: 28
<212> TYPE: PRT
<213> ORGANISM: Artificial
<220> FEATURE:
<223> OTHER INFORMATION: Synthetic FGF analog

<400> SEQUENCE: 8

Asn Arg Phe His Ser Trp Asp Cys Ile Lys Thr Trp Ala Ser Asp Thr
1               5                   10                  15

Phe Val Leu Val Cys Tyr Asp Asp Gly Ser Glu Ala
            20                  25

<210> SEQ ID NO 9
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 9

His Ile Lys Leu Gln Leu Gln Ala Glu Glu Arg Gly Val Val Ser
1               5                   10                  15

<210> SEQ ID NO 10
<211> LENGTH: 17
<212> TYPE: PRT
```

```
<213> ORGANISM: Artificial
<220> FEATURE:
<223> OTHER INFORMATION: Synthetic FGF-1 analog

<400> SEQUENCE: 10

Tyr Ile Ser Lys Lys His Ala Glu Lys Asn Trp Phe Val Gly Leu Lys
1               5                   10                  15

Lys

<210> SEQ ID NO 11
<211> LENGTH: 15
<212> TYPE: PRT
<213> ORGANISM: Artificial
<220> FEATURE:
<223> OTHER INFORMATION: Synthetic FGF-1 analog

<400> SEQUENCE: 11

His Ile Gln Leu Gln Leu Ser Ala Glu Ser Val Gly Glu Val Tyr
1               5                   10                  15

<210> SEQ ID NO 12
<211> LENGTH: 20
<212> TYPE: PRT
<213> ORGANISM: Artificial
<220> FEATURE:
<223> OTHER INFORMATION: Synthetic FGF-7 analog

<400> SEQUENCE: 12

Tyr Ala Ser Ala Lys Trp Thr His Asn Gly Gly Glu Met Phe Val Ala
1               5                   10                  15

Leu Asn Gln Lys
            20

<210> SEQ ID NO 13
<211> LENGTH: 15
<212> TYPE: PRT
<213> ORGANISM: Artificial
<220> FEATURE:
<223> OTHER INFORMATION: Syntehtic FGF-7 analog

<400> SEQUENCE: 13

Tyr Asn Ile Met Glu Ile Arg Thr Val Ala Val Gly Ile Val Ala
1               5                   10                  15

<210> SEQ ID NO 14
<211> LENGTH: 20
<212> TYPE: PRT
<213> ORGANISM: Artificial
<220> FEATURE:
<223> OTHER INFORMATION: Synthetic FGF-10 analog

<400> SEQUENCE: 14

Tyr Ala Ser Phe Asn Trp Gln His Asn Gly Arg Gln Met Tyr Val Ala
1               5                   10                  15

Leu Asn Gln Lys
            20

<210> SEQ ID NO 15
<211> LENGTH: 19
<212> TYPE: PRT
<213> ORGANISM: Artificial
<220> FEATURE:
<223> OTHER INFORMATION: Synthetic FGF-22 analog

<400> SEQUENCE: 15

Tyr Ala Ser Gln Arg Trp Arg Arg Arg Gly Gln Pro Asn Leu Ala Leu
```

```
1               5                   10                  15

Asp Arg Arg

<210> SEQ ID NO 16
<211> LENGTH: 21
<212> TYPE: PRT
<213> ORGANISM: Artificial
<220> FEATURE:
<223> OTHER INFORMATION: Synthetic FGF-9 analog

<400> SEQUENCE: 16

Tyr Ser Ser Asn Leu Tyr Lys His Val Asp Thr Gly Arg Arg Tyr Tyr
1               5                   10                  15

Val Ala Leu Asn Lys
            20

<210> SEQ ID NO 17
<211> LENGTH: 20
<212> TYPE: PRT
<213> ORGANISM: Artificial
<220> FEATURE:
<223> OTHER INFORMATION: Synthetic FGF-16 anlog

<400> SEQUENCE: 17

Tyr Ala Ser Thr Leu Tyr Lys His Ser Asp Ser Glu Arg Gln Tyr Val
1               5                   10                  15

Ala Leu Asn Lys
            20

<210> SEQ ID NO 18
<211> LENGTH: 20
<212> TYPE: PRT
<213> ORGANISM: Artificial
<220> FEATURE:
<223> OTHER INFORMATION: Synthetic FGF-20 analog

<400> SEQUENCE: 18

Tyr Ser Ser Asn Ile Tyr Lys His Gly Asp Thr Gly Arg Arg Phe Val
1               5                   10                  15

Ala Leu Asn Lys
            20

<210> SEQ ID NO 19
<211> LENGTH: 16
<212> TYPE: PRT
<213> ORGANISM: Artificial
<220> FEATURE:
<223> OTHER INFORMATION: Synthetic FGF-4 analog

<400> SEQUENCE: 19

Tyr Glu Ser Tyr Lys Tyr Pro Gly Met Phe Ile Ala Leu Ser Lys Asn
1               5                   10                  15

<210> SEQ ID NO 20
<211> LENGTH: 17
<212> TYPE: PRT
<213> ORGANISM: Artificial
<220> FEATURE:
<223> OTHER INFORMATION: Synthetic FGF-6 analog

<400> SEQUENCE: 20

Tyr Glu Ser Asp Leu Tyr Gln Gly Thr Tyr Ile Leu Ser Lys Tyr Gly
1               5                   10                  15

Arg
```

```
<210> SEQ ID NO 21
<211> LENGTH: 20
<212> TYPE: PRT
<213> ORGANISM: Artificial
<220> FEATURE:
<223> OTHER INFORMATION: Synthetic FGF-12 analog

<400> SEQUENCE: 21

Tyr Ser Ser Thr Leu Tyr Arg Gln Gln Glu Ser Gly Arg Ala Trp Phe
1               5                   10                  15

Leu Gly Asn Lys
            20

<210> SEQ ID NO 22
<211> LENGTH: 21
<212> TYPE: PRT
<213> ORGANISM: Artificial
<220> FEATURE:
<223> OTHER INFORMATION: Synthetic FGF-14 analog

<400> SEQUENCE: 22

Tyr Ser Ser Met Leu Tyr Arg Gln Gln Glu Ser Gly Arg Ala Trp Phe
1               5                   10                  15

Leu Gly Leu Asn Lys
            20

<210> SEQ ID NO 23
<211> LENGTH: 21
<212> TYPE: PRT
<213> ORGANISM: Artificial
<220> FEATURE:
<223> OTHER INFORMATION: Synthetic FGF-13 analog

<400> SEQUENCE: 23

Tyr Ser Ser Met Ile Tyr Arg Gln Gln Gln Ser Gly Arg Gly Trp Tyr
1               5                   10                  15

Leu Gly Leu Asn Lys
            20

<210> SEQ ID NO 24
<211> LENGTH: 19
<212> TYPE: PRT
<213> ORGANISM: Artificial
<220> FEATURE:
<223> OTHER INFORMATION: Synthetic FGF-11 analog

<400> SEQUENCE: 24

Tyr Ala Ser Ala Leu Tyr Arg Gln Arg Arg Ser Gly Arg Ala Trp Tyr
1               5                   10                  15

Leu Asp Lys

<210> SEQ ID NO 25
<211> LENGTH: 20
<212> TYPE: PRT
<213> ORGANISM: Artificial
<220> FEATURE:
<223> OTHER INFORMATION: Synthetic VEGF analog

<400> SEQUENCE: 25

Ala Pro Met Ala Glu Gly Gly Gly Gln Asn His His Glu Val Val Lys
1               5                   10                  15

Phe Met Asp Val
            20
```

```
<210> SEQ ID NO 26
<211> LENGTH: 11
<212> TYPE: PRT
<213> ORGANISM: Artificial
<220> FEATURE:
<223> OTHER INFORMATION: Synthetic VEGF  analog

<400> SEQUENCE: 26

Gly Ala Thr Trp Leu Pro Pro Asn Pro Thr Lys
1               5                   10

<210> SEQ ID NO 27
<211> LENGTH: 20
<212> TYPE: PRT
<213> ORGANISM: Artificial
<220> FEATURE:
<223> OTHER INFORMATION: Synthetic  VEGF analog

<400> SEQUENCE: 27

Asn Phe Leu Leu Ser Trp Val His Trp Ser Leu Ala Leu Leu Leu Tyr
1               5                   10                  15

Leu His His Ala
            20

<210> SEQ ID NO 28
<211> LENGTH: 13
<212> TYPE: PRT
<213> ORGANISM: Artificial
<220> FEATURE:
<223> OTHER INFORMATION: Synthetic BMP analog

<400> SEQUENCE: 28

Leu Tyr Val Asp Phe Ser Asp Val Gly Trp Asn Asp Trp
1               5                   10

<210> SEQ ID NO 29
<211> LENGTH: 15
<212> TYPE: PRT
<213> ORGANISM: Artificial
<220> FEATURE:
<223> OTHER INFORMATION: Synthetic BMP analog

<400> SEQUENCE: 29

Ala Ile Ser Met Leu Tyr Leu Asp Glu Asn Glu Lys Val Val Leu
1               5                   10                  15

<210> SEQ ID NO 30
<211> LENGTH: 17
<212> TYPE: PRT
<213> ORGANISM: Artificial
<220> FEATURE:
<223> OTHER INFORMATION: Synthetic BMP analog

<400> SEQUENCE: 30

Ile Ser Met Leu Tyr Leu Asp Glu Asn Glu Lys Val Val Leu Lys Asn
1               5                   10                  15

Tyr

<210> SEQ ID NO 31
<211> LENGTH: 15
<212> TYPE: PRT
<213> ORGANISM: Artificial
<220> FEATURE:
<223> OTHER INFORMATION: Synthetic BMP analog

<400> SEQUENCE: 31

Glu Lys Val Val Leu Lys Asn Tyr Gln Asp Met Val Val Glu Gly
```

-continued

```
<210> SEQ ID NO 32
<211> LENGTH: 16
<212> TYPE: PRT
<213> ORGANISM: Artificial
<220> FEATURE:
<223> OTHER INFORMATION: Synthetic BMP analog

<400> SEQUENCE: 32

Leu Val Val Lys Glu Asn Glu Asp Leu Tyr Leu Met Ser Ile Ala Cys
1               5                   10                  15

<210> SEQ ID NO 33
<211> LENGTH: 16
<212> TYPE: PRT
<213> ORGANISM: Artificial
<220> FEATURE:
<223> OTHER INFORMATION: Synthetic BMP analog

<400> SEQUENCE: 33

Ala Phe Tyr Cys His Gly Glu Cys Pro Phe Pro Leu Ala Asp His Leu
1               5                   10                  15

<210> SEQ ID NO 34
<211> LENGTH: 23
<212> TYPE: PRT
<213> ORGANISM: Artificial
<220> FEATURE:
<223> OTHER INFORMATION: Synthetic BMP analog

<400> SEQUENCE: 34

Pro Phe Pro Leu Ala Asp His Leu Asn Ser Thr Asn His Ala Ile Val
1               5                   10                  15

Gln Thr Leu Val Asn Ser Val
            20

<210> SEQ ID NO 35
<211> LENGTH: 21
<212> TYPE: PRT
<213> ORGANISM: Artificial
<220> FEATURE:
<223> OTHER INFORMATION: Synthetic TGF-beta1 analog

<400> SEQUENCE: 35

Ile Val Tyr Tyr Val Gly Arg Lys Pro Lys Val Glu Gln Leu Ser Asn
1               5                   10                  15

Met Ile Val Arg Ser
            20

<210> SEQ ID NO 36
<211> LENGTH: 22
<212> TYPE: PRT
<213> ORGANISM: Artificial
<220> FEATURE:
<223> OTHER INFORMATION: Synthetic TGF-beta2  analog

<400> SEQUENCE: 36

Thr Ile Leu Tyr Tyr Ile Gly Lys Thr Pro Lys Ile Glu Gln Leu Ser
1               5                   10                  15

Asn Met Ile Val Lys Ser
            20

<210> SEQ ID NO 37
<211> LENGTH: 21
<212> TYPE: PRT
```

-continued

```
<213> ORGANISM: Artificial
<220> FEATURE:
<223> OTHER INFORMATION: Synthetic TGF-beta3 analog

<400> SEQUENCE: 37

Leu Thr Ile Leu Tyr Tyr Val Gly Arg Thr Pro Lys Val Glu Gln Leu
1               5                   10                  15

Ser Asn Met Val Val
            20

<210> SEQ ID NO 38
<211> LENGTH: 23
<212> TYPE: PRT
<213> ORGANISM: Artificial
<220> FEATURE:
<223> OTHER INFORMATION: Synthetic BMP-2 analog

<400> SEQUENCE: 38

Ala Ile Ser Met Leu Tyr Leu Asp Glu Asn Glu Lys Val Val Leu Lys
1               5                   10                  15

Asn Tyr Gln Asp Met Val Val
            20

<210> SEQ ID NO 39
<211> LENGTH: 24
<212> TYPE: PRT
<213> ORGANISM: Artificial
<220> FEATURE:
<223> OTHER INFORMATION: Synthetic BMP-3 analog

<400> SEQUENCE: 39

Ser Ser Leu Ser Ile Leu Phe Phe Asp Glu Asn Lys Asn Val Val Leu
1               5                   10                  15

Lys Val Tyr Pro Asn Met Thr Val
            20

<210> SEQ ID NO 40
<211> LENGTH: 24
<212> TYPE: PRT
<213> ORGANISM: Artificial
<220> FEATURE:
<223> OTHER INFORMATION: Synthetic BMP-3beta analog

<400> SEQUENCE: 40

Asn Ser Leu Gly Val Leu Phe Leu Asp Glu Asn Arg Asn Val Val Leu
1               5                   10                  15

Lys Val Tyr Pro Asn Met Ser Val
            20

<210> SEQ ID NO 41
<211> LENGTH: 23
<212> TYPE: PRT
<213> ORGANISM: Artificial
<220> FEATURE:
<223> OTHER INFORMATION: Synthetic BMP-4 analog

<400> SEQUENCE: 41

Ala Ile Ser Met Leu Tyr Leu Asp Glu Tyr Asp Lys Val Val Leu Lys
1               5                   10                  15

Asn Tyr Gln Glu Met Val Val
            20

<210> SEQ ID NO 42
<211> LENGTH: 23
<212> TYPE: PRT
```

```
<213> ORGANISM: Artificial
<220> FEATURE:
<223> OTHER INFORMATION: Synthetic BMP-5 analog

<400> SEQUENCE: 42

Ala Ile Ser Val Leu Tyr Phe Asp Asp Ser Ser Asn Val Ile Leu Lys
1               5                   10                  15

Lys Tyr Arg Asn Met Val Val
            20

<210> SEQ ID NO 43
<211> LENGTH: 23
<212> TYPE: PRT
<213> ORGANISM: Artificial
<220> FEATURE:
<223> OTHER INFORMATION: Synthetic BMP-6 analog

<400> SEQUENCE: 43

Ala Ile Ser Val Leu Tyr Phe Asp Asp Asn Ser Asn Val Ile Leu Lys
1               5                   10                  15

Lys Tyr Arg Asn Met Val Val
            20

<210> SEQ ID NO 44
<211> LENGTH: 23
<212> TYPE: PRT
<213> ORGANISM: Artificial
<220> FEATURE:
<223> OTHER INFORMATION: Synthetic BMP-7 analog

<400> SEQUENCE: 44

Ala Ile Ser Val Leu Tyr Phe Asp Asp Ser Ser Asn Val Ile Leu Lys
1               5                   10                  15

Lys Tyr Arg Asn Met Val Val
            20

<210> SEQ ID NO 45
<211> LENGTH: 23
<212> TYPE: PRT
<213> ORGANISM: Artificial
<220> FEATURE:
<223> OTHER INFORMATION: Synthetic BMP-8 analog

<400> SEQUENCE: 45

Ala Thr Ser Val Leu Tyr Tyr Asp Ser Ser Asn Asn Val Ile Leu Arg
1               5                   10                  15

Lys Ala Arg Asn Met Val Val
            20

<210> SEQ ID NO 46
<211> LENGTH: 23
<212> TYPE: PRT
<213> ORGANISM: Artificial
<220> FEATURE:
<223> OTHER INFORMATION: Synthetic BMP-9 analog

<400> SEQUENCE: 46

Ile Ser Val Leu Tyr Lys Asp Asp Met Gly Val Pro Thr Leu Lys Tyr
1               5                   10                  15

His Tyr Glu Gly Met Ser Val
            20

<210> SEQ ID NO 47
<211> LENGTH: 22
<212> TYPE: PRT
```

```
<213> ORGANISM: Artificial
<220> FEATURE:
<223> OTHER INFORMATION: Synthetic BMP-10 analog

<400> SEQUENCE: 47

Ile Ser Ile Leu Tyr Leu Asp Lys Gly Val Val Thr Tyr Lys Phe Lys
1               5                   10                  15

Tyr Glu Gly Met Ala Val
            20

<210> SEQ ID NO 48
<211> LENGTH: 22
<212> TYPE: PRT
<213> ORGANISM: Artificial
<220> FEATURE:
<223> OTHER INFORMATION: Synthetic BMP-11 analog

<400> SEQUENCE: 48

Ile Asn Met Leu Tyr Phe Asn Asp Lys Gln Gln Ile Ile Tyr Gly Lys
1               5                   10                  15

Ile Pro Gly Met Val Val
            20

<210> SEQ ID NO 49
<211> LENGTH: 22
<212> TYPE: PRT
<213> ORGANISM: Artificial
<220> FEATURE:
<223> OTHER INFORMATION: Synthetic BMP-12 analog

<400> SEQUENCE: 49

Ile Ser Ile Leu Tyr Ile Asp Ala Ala Asn Asn Val Val Tyr Lys Gln
1               5                   10                  15

Tyr Glu Asp Met Val Val
            20

<210> SEQ ID NO 50
<211> LENGTH: 22
<212> TYPE: PRT
<213> ORGANISM: artificial
<220> FEATURE:
<223> OTHER INFORMATION: Synthetic BMP-13 analog

<400> SEQUENCE: 50

Ile Ser Ile Leu Tyr Ile Asp Ala Gly Asn Asn Val Val Tyr Lys Gln
1               5                   10                  15

Tyr Glu Asp Met Val Val
            20

<210> SEQ ID NO 51
<211> LENGTH: 22
<212> TYPE: PRT
<213> ORGANISM: Artificial
<220> FEATURE:
<223> OTHER INFORMATION: Synthetic BMP-14 analog

<400> SEQUENCE: 51

Ile Ser Ile Leu Phe Ile Asp Ser Ala Asn Asn Val Val Tyr Lys Gln
1               5                   10                  15

Tyr Glu Asp Met Val Val
            20

<210> SEQ ID NO 52
<211> LENGTH: 22
<212> TYPE: PRT
```

```
<213> ORGANISM: Artificial
<220> FEATURE:
<223> OTHER INFORMATION: Synthetic BMP-15 analog

<400> SEQUENCE: 52

Ile Ser Val Leu Met Ile Glu Ala Asn Gly Ser Ile Leu Tyr Lys Glu
1               5                   10                  15

Tyr Glu Gly Met Ile Ala
            20

<210> SEQ ID NO 53
<211> LENGTH: 22
<212> TYPE: PRT
<213> ORGANISM: Artificial
<220> FEATURE:
<223> OTHER INFORMATION: Synthetic GDF-1 analog

<400> SEQUENCE: 53

Ile Ser Val Leu Phe Phe Asp Asn Ser Asp Asn Val Val Leu Arg Gln
1               5                   10                  15

Tyr Glu Asp Met Val Val
            20

<210> SEQ ID NO 54
<211> LENGTH: 22
<212> TYPE: PRT
<213> ORGANISM: Artificial
<220> FEATURE:
<223> OTHER INFORMATION: Synthetic GDF-3 analog

<400> SEQUENCE: 54

Ile Ser Met Leu Tyr Gln Asp Asn Asn Asp Asn Val Ile Leu Arg His
1               5                   10                  15

Tyr Glu Asp Met Val Val
            20

<210> SEQ ID NO 55
<211> LENGTH: 22
<212> TYPE: PRT
<213> ORGANISM: Artificial
<220> FEATURE:
<223> OTHER INFORMATION: Synthetic GDF-8 analog

<400> SEQUENCE: 55

Ile Asn Met Tyr Leu Phe Asn Gly Lys Glu Gln Ile Ile Tyr Gly Lys
1               5                   10                  15

Ile Pro Ala Met Val Val
            20

<210> SEQ ID NO 56
<211> LENGTH: 22
<212> TYPE: PRT
<213> ORGANISM: Artificial
<220> FEATURE:
<223> OTHER INFORMATION: Synthetic GDF-9 analog

<400> SEQUENCE: 56

Leu Ser Val Leu Thr Ile Glu Pro Asp Gly Ser Ile Ala Tyr Lys Glu
1               5                   10                  15

Tyr Glu Asp Met Ile Ala
            20

<210> SEQ ID NO 57
<211> LENGTH: 15
<212> TYPE: PRT
```

```
<213> ORGANISM: Artificial
<220> FEATURE:
<223> OTHER INFORMATION: Synthetic BMP analog

<400> SEQUENCE: 57

Leu Val Val Lys Glu Asn Glu Asp Leu Tyr Leu Met Ser Ile Ala
1               5                   10                  15

<210> SEQ ID NO 58
<211> LENGTH: 17
<212> TYPE: PRT
<213> ORGANISM: Artificial
<220> FEATURE:
<223> OTHER INFORMATION: Synthetic BMP analog

<400> SEQUENCE: 58

Tyr Asn Lys Leu Val Val Lys Glu Asn Glu Asp Leu Tyr Leu Met Ser
1               5                   10                  15

Ile

<210> SEQ ID NO 59
<211> LENGTH: 13
<212> TYPE: PRT
<213> ORGANISM: Artificial
<220> FEATURE:
<223> OTHER INFORMATION: Synthetic BMP analog

<400> SEQUENCE: 59

Lys Lys Leu Ile Val Asn Ser Ser Glu Asp Phe Tyr Leu
1               5                   10

<210> SEQ ID NO 60
<211> LENGTH: 13
<212> TYPE: PRT
<213> ORGANISM: Artificial
<220> FEATURE:
<223> OTHER INFORMATION: Synthetic BMP analog

<400> SEQUENCE: 60

Trp Asp Asn Trp Gly Val Asp Ser Phe Asp Val Tyr Leu
1               5                   10

<210> SEQ ID NO 61
<211> LENGTH: 15
<212> TYPE: PRT
<213> ORGANISM: Artificial
<220> FEATURE:
<223> OTHER INFORMATION: Synthetic BMP analog

<400> SEQUENCE: 61

Gly Glu Val Val Met Asp Gln Tyr Asn Lys Leu Val Val Lys Glu
1               5                   10                  15

<210> SEQ ID NO 62
<211> LENGTH: 16
<212> TYPE: PRT
<213> ORGANISM: Artificial
<220> FEATURE:
<223> OTHER INFORMATION: Synthetic BMP analog

<400> SEQUENCE: 62

Leu His Asp Ala Leu Pro Phe Pro Cys Glu Gly His Cys Tyr Phe Ala
1               5                   10                  15

<210> SEQ ID NO 63
<211> LENGTH: 23
<212> TYPE: PRT
```

```
<213> ORGANISM: Artificial
<220> FEATURE:
<223> OTHER INFORMATION: Synthetic BMP analog

<400> SEQUENCE: 63

Val Ser Asn Val Leu Thr Gln Val Ile Ala His Asn Thr Ser Asn Leu
1               5                   10                  15

His Asp Ala Leu Pro Phe Pro
            20

<210> SEQ ID NO 64
<211> LENGTH: 16
<212> TYPE: PRT
<213> ORGANISM: Artificial
<220> FEATURE:
<223> OTHER INFORMATION: Synthetic BMP analog

<400> SEQUENCE: 64

Leu Val Val Lys Glu Asn Glu Asp Leu Tyr Leu Met Ser Ile Ala Cys
1               5                   10                  15

<210> SEQ ID NO 65
<211> LENGTH: 10
<212> TYPE: PRT
<213> ORGANISM: Artificial
<220> FEATURE:
<223> OTHER INFORMATION: Synthetic FGF-1 analog

<400> SEQUENCE: 65

Ser Asn Gly Gly His Phe Leu Arg Ile Leu
1               5                   10

<210> SEQ ID NO 66
<211> LENGTH: 10
<212> TYPE: PRT
<213> ORGANISM: Artificial
<220> FEATURE:
<223> OTHER INFORMATION: Synthetic FGF-2 analog

<400> SEQUENCE: 66

Lys Asn Gly Gly Phe Phe Leu Arg Ile His
1               5                   10

<210> SEQ ID NO 67
<211> LENGTH: 9
<212> TYPE: PRT
<213> ORGANISM: Artificial
<220> FEATURE:
<223> OTHER INFORMATION: Synthetic FGF-7 analog

<400> SEQUENCE: 67

Arg Thr Gln Trp Tyr Leu Arg Ile Asp
1               5

<210> SEQ ID NO 68
<211> LENGTH: 9
<212> TYPE: PRT
<213> ORGANISM: Artificial
<220> FEATURE:
<223> OTHER INFORMATION: Synthetic FGF-10 analog

<400> SEQUENCE: 68

Phe Thr Lys Tyr Phe Leu Lys Ile Glu
1               5

<210> SEQ ID NO 69
<211> LENGTH: 9
```

```
<212> TYPE: PRT
<213> ORGANISM: Artificial
<220> FEATURE:
<223> OTHER INFORMATION: Synthetic FGF-22 analog

<400> SEQUENCE: 69

Ser Thr His Phe Phe Leu Arg Val Asp
1               5

<210> SEQ ID NO 70
<211> LENGTH: 9
<212> TYPE: PRT
<213> ORGANISM: Artificial
<220> FEATURE:
<223> OTHER INFORMATION: Synthetic FGF-9 analog

<400> SEQUENCE: 70

Arg Thr Gly Phe His Leu Glu Ile Phe
1               5

<210> SEQ ID NO 71
<211> LENGTH: 9
<212> TYPE: PRT
<213> ORGANISM: Artificial
<220> FEATURE:
<223> OTHER INFORMATION: Synthetic FGF-16 analog

<400> SEQUENCE: 71

Arg Thr Gly Phe His Leu Glu Ile Phe
1               5

<210> SEQ ID NO 72
<211> LENGTH: 9
<212> TYPE: PRT
<213> ORGANISM: Artificial
<220> FEATURE:
<223> OTHER INFORMATION: Synthetic FGF-20 analog

<400> SEQUENCE: 72

Arg Thr Gly Phe His Leu Gln Ile Leu
1               5

<210> SEQ ID NO 73
<211> LENGTH: 11
<212> TYPE: PRT
<213> ORGANISM: Artificial
<220> FEATURE:
<223> OTHER INFORMATION: Synthetic FGF-4 analog

<400> SEQUENCE: 73

Asn Val Gly Ile Gly Phe His Leu Gln Ala Leu
1               5                   10

<210> SEQ ID NO 74
<211> LENGTH: 11
<212> TYPE: PRT
<213> ORGANISM: Artificial
<220> FEATURE:
<223> OTHER INFORMATION: Synthetic FGF-6 analog

<400> SEQUENCE: 74

Asn Val Gly Ile Gly Phe His Leu Gln Val Leu
1               5                   10

<210> SEQ ID NO 75
<211> LENGTH: 9
<212> TYPE: PRT
<213> ORGANISM: Artificial
```

```
<220> FEATURE:
<223> OTHER INFORMATION: Synthetic FGF-12 analog

<400> SEQUENCE: 75

Gln Gln Gly Tyr Phe Leu Gln Met His
1               5

<210> SEQ ID NO 76
<211> LENGTH: 9
<212> TYPE: PRT
<213> ORGANISM: Artificial
<220> FEATURE:
<223> OTHER INFORMATION: Synthetic FGF-14 analog

<400> SEQUENCE: 76

Arg Gln Gly Tyr Tyr Leu Gln Met His
1               5

<210> SEQ ID NO 77
<211> LENGTH: 9
<212> TYPE: PRT
<213> ORGANISM: Artificial
<220> FEATURE:
<223> OTHER INFORMATION: Synthetic FGF-13 analog

<400> SEQUENCE: 77

Arg Gln Gly Tyr His Leu Gln Leu Gln
1               5

<210> SEQ ID NO 78
<211> LENGTH: 9
<212> TYPE: PRT
<213> ORGANISM: Artificial
<220> FEATURE:
<223> OTHER INFORMATION: Synthetic FGF-11 analog

<400> SEQUENCE: 78

Arg Gln Gly Phe Tyr Leu Gln Ala Asn
1               5

<210> SEQ ID NO 79
<211> LENGTH: 10
<212> TYPE: PRT
<213> ORGANISM: Artificial
<220> FEATURE:
<223> OTHER INFORMATION: Synthetic FGF-8 analog

<400> SEQUENCE: 79

Arg Thr Ser Gly Lys His Val Gln Val Leu
1               5                   10

<210> SEQ ID NO 80
<211> LENGTH: 10
<212> TYPE: PRT
<213> ORGANISM: Artificial
<220> FEATURE:
<223> OTHER INFORMATION: Synthetic FGF-17 analog

<400> SEQUENCE: 80

Arg Thr Ser Gly Lys His Val Gln Val Thr
1               5                   10

<210> SEQ ID NO 81
<211> LENGTH: 10
<212> TYPE: PRT
<213> ORGANISM: Artificial
<220> FEATURE:
<223> OTHER INFORMATION: Synthetic FGF-18 analog
```

-continued

```
<400> SEQUENCE: 81

Arg Thr Ser Gly Lys His Ile Gln Val Leu
1               5                   10

<210> SEQ ID NO 82
<211> LENGTH: 9
<212> TYPE: PRT
<213> ORGANISM: Artificial
<220> FEATURE:
<223> OTHER INFORMATION: Synthetic FGF-3 analog

<400> SEQUENCE: 82

Ala Thr Lys Tyr His Leu Gln Leu His
1               5

<210> SEQ ID NO 83
<211> LENGTH: 11
<212> TYPE: PRT
<213> ORGANISM: Artificial
<220> FEATURE:
<223> OTHER INFORMATION: Synthetic FGF-5 analog

<400> SEQUENCE: 83

Arg Val Gly Ile Gly Phe His Leu Gln Ile Tyr
1               5                   10

<210> SEQ ID NO 84
<211> LENGTH: 14
<212> TYPE: PRT
<213> ORGANISM: Artificial
<220> FEATURE:
<223> OTHER INFORMATION: Synthetic FGF-19 analog

<400> SEQUENCE: 84

Ser Gly Pro His Gly Leu Ser Ser Cys Phe Leu Arg Ile Arg
1               5                   10

<210> SEQ ID NO 85
<211> LENGTH: 13
<212> TYPE: PRT
<213> ORGANISM: Artificial
<220> FEATURE:
<223> OTHER INFORMATION: Synthetic FGF-21 analog

<400> SEQUENCE: 85

Asp Asp Ala Gln Gln Thr Glu Ala His Leu Glu Ile Arg
1               5                   10

<210> SEQ ID NO 86
<211> LENGTH: 12
<212> TYPE: PRT
<213> ORGANISM: Artificial
<220> FEATURE:
<223> OTHER INFORMATION: Synthetic FGF-23 analog

<400> SEQUENCE: 86

Ala Thr Ala Arg Asn Ser Tyr His Leu Gln Ile His
1               5                   10

<210> SEQ ID NO 87
<211> LENGTH: 27
<212> TYPE: PRT
<213> ORGANISM: Artificial
<220> FEATURE:
<223> OTHER INFORMATION: Synthetic BMP analog

<400> SEQUENCE: 87
```

-continued

```
Thr Gln Leu Asn Ala Ile Ser Val Leu Tyr Phe Asp Asp Ser Asn
1               5                   10                  15

Val Ile Leu Lys Lys Tyr Arg Asn Met Val Val
                20                  25

<210> SEQ ID NO 88
<211> LENGTH: 25
<212> TYPE: PRT
<213> ORGANISM: Artificial
<220> FEATURE:
<223> OTHER INFORMATION: Synthetic BMP analog

<400> SEQUENCE: 88

His Glu Leu Tyr Val Ser Phe Arg Asp Leu Gly Trp Gln Asp Trp Ile
1               5                   10                  15

Ile Ala Pro Glu Gly Tyr Ala Ala Tyr
                20                  25

<210> SEQ ID NO 89
<211> LENGTH: 14
<212> TYPE: PRT
<213> ORGANISM: Artificial
<220> FEATURE:
<223> OTHER INFORMATION: Synthetic Avinin-A analog

<400> SEQUENCE: 89

Ser Met Leu Tyr Tyr Asp Asp Gly Gln Asn Ile Ile Lys Lys
1               5                   10

<210> SEQ ID NO 90
<211> LENGTH: 14
<212> TYPE: PRT
<213> ORGANISM: Artificial
<220> FEATURE:
<223> OTHER INFORMATION: Synthetic Avinin-A analog

<400> SEQUENCE: 90

Lys Lys Ile Ile Asn Gln Gly Asp Asp Tyr Tyr Leu Met Ser
1               5                   10

<210> SEQ ID NO 91
<211> LENGTH: 16
<212> TYPE: PRT
<213> ORGANISM: Artificial
<220> FEATURE:
<223> OTHER INFORMATION: Synthetic Avinin-A analog

<400> SEQUENCE: 91

Ser Met Leu Tyr Tyr Asp Asp Gly Gln Asn Ile Ile Lys Lys Asp Ile
1               5                   10                  15

<210> SEQ ID NO 92
<211> LENGTH: 20
<212> TYPE: PRT
<213> ORGANISM: Artificial
<220> FEATURE:
<223> OTHER INFORMATION: Synthetic G-CSF analog

<400> SEQUENCE: 92

Ala Ser Ser Leu Pro Gln Ser Phe Leu Leu Lys Cys Leu Glu Gln Val
1               5                   10                  15

Arg Lys Ile Gln
                20

<210> SEQ ID NO 93
```

```
<211> LENGTH: 17
<212> TYPE: PRT
<213> ORGANISM: Artificial
<220> FEATURE:
<223> OTHER INFORMATION: Synthetic G-CSF analog

<400> SEQUENCE: 93

Leu Asp Val Ala Asp Phe Ala Thr Thr Ile Trp Gln Gln Met Glu Glu
1               5                   10                  15
Leu

<210> SEQ ID NO 94
<211> LENGTH: 11
<212> TYPE: PRT
<213> ORGANISM: Artificial
<220> FEATURE:
<223> OTHER INFORMATION: Synthetic G-CSF analog

<400> SEQUENCE: 94

Tyr Lys Leu Ala His Pro Glu Glu Leu Val Leu
1               5                   10

<210> SEQ ID NO 95
<211> LENGTH: 16
<212> TYPE: PRT
<213> ORGANISM: Artificial
<220> FEATURE:
<223> OTHER INFORMATION: Synthetic GM-CSF analog

<400> SEQUENCE: 95

Trp Glu His Val Asn Ala Ile Gln Glu Ala Arg Arg Leu Leu Asn Leu
1               5                   10                  15

<210> SEQ ID NO 96
<211> LENGTH: 33
<212> TYPE: PRT
<213> ORGANISM: Artificial
<220> FEATURE:
<223> OTHER INFORMATION: Synthetic GM-CSF analog

<400> SEQUENCE: 96

Leu Gln Thr Arg Leu Glu Leu Tyr Lys Gln Gly Leu Arg Gly Ser Leu
1               5                   10                  15
Thr Lys Leu Lys Gly Pro Leu Thr Met Met Ala Ser His Tyr Lys Gln
                20                  25                  30
His

<210> SEQ ID NO 97
<211> LENGTH: 13
<212> TYPE: PRT
<213> ORGANISM: Artificial
<220> FEATURE:
<223> OTHER INFORMATION: Synthetic GM-CSF analog

<400> SEQUENCE: 97

Ser Phe Lys Glu Asn Leu Lys Asp Phe Leu Leu Val Ile
1               5                   10

<210> SEQ ID NO 98
<211> LENGTH: 15
<212> TYPE: PRT
<213> ORGANISM: Artificial
<220> FEATURE:
<223> OTHER INFORMATION: Synthetic IFN-bata analog

<400> SEQUENCE: 98
```

Ser Val Gln Ala Arg Trp Glu Ala Ala Phe Asp Leu Asp Leu Tyr
1               5                   10                  15

<210> SEQ ID NO 99
<211> LENGTH: 15
<212> TYPE: PRT
<213> ORGANISM: Artificial
<220> FEATURE:
<223> OTHER INFORMATION: Synthetic IFN-beta analog

<400> SEQUENCE: 99

Tyr Leu Asp Leu Asp Phe Ala Ala Glu Trp Arg Ala Gln Val Ser
1               5                   10                  15

<210> SEQ ID NO 100
<211> LENGTH: 15
<212> TYPE: PRT
<213> ORGANISM: Artificial
<220> FEATURE:
<223> OTHER INFORMATION: Synthetic IFN-bata analog

<400> SEQUENCE: 100

Ser Ser Ser Thr Gly Trp Asn Glu Thr Ile Val Glu Asn Leu Ile
1               5                   10                  15

<210> SEQ ID NO 101
<211> LENGTH: 24
<212> TYPE: PRT
<213> ORGANISM: Artificial
<220> FEATURE:
<223> OTHER INFORMATION: Synthetic PDGF analog

<400> SEQUENCE: 101

Lys Thr Arg Thr Glu Val Phe Glu Ile Ser Arg Arg Leu Ile Asp Arg
1               5                   10                  15

Thr Asn Ala Asn Phe Leu Val Trp
            20

<210> SEQ ID NO 102
<211> LENGTH: 16
<212> TYPE: PRT
<213> ORGANISM: Artificial
<220> FEATURE:
<223> OTHER INFORMATION: Synthetic PDGF analog

<400> SEQUENCE: 102

Gln Val Arg Lys Ile Glu Ile Val Arg Lys Lys Pro Ile Phe Lys Lys
1               5                   10                  15

<210> SEQ ID NO 103
<211> LENGTH: 19
<212> TYPE: PRT
<213> ORGANISM: Artificial
<220> FEATURE:
<223> OTHER INFORMATION: Synthetic SDF-1 analog

<400> SEQUENCE: 103

Lys Pro Val Ser Leu Ser Tyr Arg Cys Pro Cys Arg Phe Phe Glu Ser
1               5                   10                  15

His Val Ala

<210> SEQ ID NO 104
<211> LENGTH: 9
<212> TYPE: PRT
<213> ORGANISM: Artificial
<220> FEATURE:
<223> OTHER INFORMATION: Synthetic SDF-1 ananlog

```
<400> SEQUENCE: 104

Lys Trp Ile Gln Glu Tyr Leu Glu Lys
1               5

<210> SEQ ID NO 105
<211> LENGTH: 13
<212> TYPE: PRT
<213> ORGANISM: Artificial
<220> FEATURE:
<223> OTHER INFORMATION: Synthetic BMP analog

<400> SEQUENCE: 105

Ala Ile Ser Met Leu Tyr Leu Asp Glu Lys Val Val Leu
1               5                   10

<210> SEQ ID NO 106
<211> LENGTH: 13
<212> TYPE: PRT
<213> ORGANISM: Artificial
<220> FEATURE:
<223> OTHER INFORMATION: Synthetic BMP analog

<400> SEQUENCE: 106

Leu Tyr Phe Asp Glu Ser Ser Asn Val Ile Leu Lys Lys
1               5                   10

<210> SEQ ID NO 107
<211> LENGTH: 11
<212> TYPE: PRT
<213> ORGANISM: Artificial
<220> FEATURE:
<223> OTHER INFORMATION: Synthetic PDGF-BB analog

<400> SEQUENCE: 107

Cys Val Arg Lys Ile Glu Ile Val Arg Lys Lys
1               5                   10
```

SINGLE BRANCH HEPARIN-BINDING GROWTH FACTOR ANALOGS

CROSS-REFERENCE TO RELATED APPLICATIONS

This application is a continuation application of U.S. patent application Ser. No. 11/359,173, entitled Single Branch Heparin-Binding Growth Factor Analogs, filed on Feb. 21, 2006 which claims priority to and the benefit of U.S. Provisional Patent Application Ser. No. 60/655,570 entitled Single Branch Heparin Binding Growth Factor filed on Feb. 22, 2005 and the specification and claims thereof are incorporated herein by reference.

REFERENCE TO A SEQUENCE LISTING, A TABLE, OR COMPUTER PROGRAM

Applicant hereby submits a sequence listing as a text file titled 30817-singleHBGFA_ST25.txt created on May 24, 2010 having 27 kbytes that is ASCII compliant.

INTRODUCTION

The invention relates to the field of synthetic peptides and analogs of heparin-binding growth factors, including homodimeric synthetic heparin-binding growth factor analogs wherein two sequences are branched from a single branch point, the single branch point including at least one trifunctional amino acid residues, which branch point is further covalently bonded to a heparin-binding sequence. The invention further relates to the clinical uses of such analogs as soluble drugs and as coatings for medical devices.

BACKGROUND OF THE INVENTION

Note that the following discussion refers to a number of publications by author(s) and year of publication. Discussion of such publications herein is given for more complete background and is not to be construed as an admission that such publications are prior art for patentability determination purposes.

The heparin-binding growth factors (HBGFs) constitute a large class of growth factors that includes the 23 fibroblast growth factors identified to date (FGFs 1-23), HBBM (heparin-binding brain mitogen), HB-GAF (heparin-binding growth associated factor), HB-EGF (heparin-binding EGF-like factor) HB-GAM (heparin-binding growth associated molecule), TGF-α (transforming growth factor-α), TGF-βs (transforming growth factor-βs), PDGF (platelet-derived growth factor), EGF (epidermal growth factor), VEGF (vascular endothelial growth factor), IGF-1 (insulin-like growth factor-1), IGF-2 (insulin-like growth factor-2), HGF (hepatocyte growth factor), IL-1 (interleukin-1), IL-2 (interleukin-2), IFN-α (interferon-α), IFN-γ (interferon-γ), TNF-α (tumor necrosis factor-α), SDGF (Schwannoma-derived growth factor) and the many other growth factors, cytokines, lymphokines and chemokines that have an affinity for heparin.

Peptides from natural HBGFs that bind heparin-binding growth factor receptors have been identified. See for example Ray et al., Proc. Natl. Acad. Sci. USA 94:7047-7052 (1997). These authors demonstrated that two amino acid sequences from FGF-2 are sufficient to block the mitogenic activity of FGF-2 on neural progenitor cells. The first peptide is a ten amino acid sequence, from amino acids 65-74, the second peptide extends from amino acids 115-129.

In an alternative approach, an artificial peptide that binds a heparin-binding growth factor receptor (HBGFR) was identified by a phage display method. Ballinger et al., Nature BioTechnology 17:1199-1204 (1999) used this technique to isolate a 28 amino acid peptide called C19, binds FGF-2 receptors, but by itself fails to stimulate biological activity. The peptide has no amino acid sequence identity with any known FGF.

HBGFs useful in prevention or therapy of a wide range of diseases and disorders may be purified from natural sources or produced by recombinant DNA methods, however, such preparations are expensive and generally difficult to prepare.

Some efforts have been made to generate heparin-binding growth factor analogs. For example, natural PDGF occurs as an A chain and a B chain arranged in head-to-head (AA or BB) homodimers, or (AB or BA) heterodimers. Thus, U.S. Pat. No. 6,350,731 to Jehanli et al. discloses PDGF analogs in which two synthetic PDGF receptor-binding domains are covalently linked through a polyglycine or an N-(4-carboxycyclohexylmethyl)-maleimide (SMCC) chain to mimic the natural active polypeptide dimer.

U.S. Pat. No. 6,235,716 to Ben-Sasson discloses analogs of angiogenic factors. The analogs are branched multivalent ligands that include two or more angiogenic homology regions connected by a multilinker backbone.

U.S. Pat. No. 5,770,704 (the '704 patent) to Godowski discloses conjugates for activating receptor tyrosine kinases, cytokine receptors and members of the nerve growth factor receptor superfamily. The conjugates include at least two ligands capable of binding to the cognate receptor, so that the binding of the respective ligands induces oligomerization of these receptors. The ligands disclosed in the '704 patent are linked by covalent attachment to various nonproteinaceous polymers, particularly hydrophilic polymers, such as polyvinylalcohol and polyvinylpyrrolidone, and the polyvinylalkene ethers, including polyethylene glycol and polypropylene glycol. The ligands include hepatocyte growth factor (HGF) peptide variants that each bind HGF receptor, thereby causing receptor dimerization and activation of the biological activity of the HGF receptor dimer.

U.S. Pat. No. 6,284,503 (the '503 patent) to Caldwell et al. discloses a composition and method for regulating the adhesion of cells and biomolecules to hydrophobic surfaces and hydrophobic coated surfaces for cell adhesion, cell growth, cell sorting and biological assays. The composition is a biomolecule conjugated to a reactive end group activated polymer. The end group activated polymer includes a block copolymer surfactant backbone and an activation or reactive group. The block copolymer may be any surfactant having a hydrophobic region capable of adsorbing onto a hydrophobic surface, and a hydrophilic region which extends away from the surface when the hydrophobic region is adsorbed onto the hydrophobic surface. The '503 patent discloses that the biomolecules that may be conjugated to the end group activated polymer include natural or recombinant growth factors, such as PDGF, EGF, TGFα, TGFβ, NGF, IGF-I, IGF-II, GH and GHRF, as well as multi-CSF(II-3), GM-CSF, G-CSF, and M-CSF.

Other workers have described compositions that include homologs and analogs of fibroblast growth factors (FGFs). See for example U.S. Pat. No. 5,679,673 to Lappi and Baird; U.S. Pat. No. 5,989,866 to Deisher et al. and U.S. Pat. No. 6,294,359 to Fiddes et al. These disclosures relate to FGF homologs or analogs that are either conjugated to a toxic moiety and are targeted to the FGF receptor-bearing cells; or are homologs or analogs that modulate the biological pathways through the signal transduced by the FGF receptor upon binding by the FGF homolog or analog.

A series of patent applications to Kochendoerfer et al. disclose polymer-modified proteins, including synthetic chemokines and erythropoiesis stimulating proteins. See, for example, International Publications WO 02/04105, WO 02/19963 and WO 02/20033. These include chemically ligated peptide segments of a polypeptide chain of a synthetic erythropoiesis protein, such that a polypeptide chain results, with a water soluble polymer attached at one or more glycosylation sites on the protein. These applications also disclose synthetic chemokines, which are also polymer modified, and are asserted to be antagonists. However, heparin-binding domains are not disclosed. Other erythropoietin mimetics are known, such as those disclosed in U.S. Pat. Nos. 5,773,569 and 5,830,851 to Wrighton et al.

International Publication WO 00/18921 to Ballinger and Kavanaugh discloses a composition consisting of fusion proteins having FGF receptor affinity linked to an "oligomerization domain", either directly or through a linking group. The oligomerization domain ranges in length from about 20 to 300 residues, and includes constructs such as transcription factors, Fc portions of IgG, leucine zippers and the like. The oligomerization domains disclosed are homodimeric domains, wherein a single FGF receptor affinity fusion protein is linked to a single domain, such as a leucine zipper, which in turn is linked to a similar molecule by means of cysteine residues at both the amino and carboxy termini of the leucine zippers, such that two parallel leucine zippers, each with a single FGF receptor affinity fusion protein, are cross-linked by means of disulfide bonds. It is also disclosed that fusion proteins may include a heparin binding domain, such as the use of jun as a multimerization domain, which is asserted to be a heparin binding domain. Thus the compositions disclosed by Ballinger and Kavanaugh are all composed of a single receptor-binding sequence covalently attached to an oligomerization domain, whereby two or more similar oligomerization domains, each with a single receptor-binding sequence, are conjoined by means of either an association provided by the oligomerization domain, or alternatively, are chemically cross-linked to provide for the covalent bonding of the individual components. A series of applications with some inventors in common, including U.S. patent application Ser. No. 10/644,703, entitled Synthetic Heparin-Binding Growth Factor Analogs, filed on Aug. 19, 2003, and U.S. patent application Ser. No. 10/224,268, entitled Synthetic Heparin-Binding Growth Factor Analogs, filed on Aug. 20, 2002, disclose constructs in which two receptor-binding domains are linked to side chains or a terminal group and a side chain of two different amino acid residues.

The above described homologs, analogs, conjugates or ligands each include a receptor-binding domain. However, none of the disclosed compositions further include two receptor-binding domains linked to a single residue through a terminal group and a side chain group of the single residue. There is still a need for new peptide analogs of HBGFs, particularly for those that function as agonists, and preferably those that contain two receptor-binding domains specific for a HBGFR. In particular, there is still a need for cost-effective synthetic peptide agonists of heparin-binding growth factor receptors, particularly synthetic heparin-binding growth factor agonists useful for coating medical devices and as soluble biologics, and as pharmaceutical agents for treating a variety of conditions.

SUMMARY OF THE INVENTION

One aspect of the present invention is a heparin-binding growth factor analog of formula I:

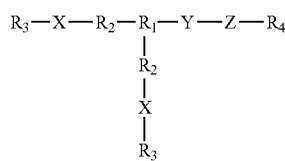

wherein:
each X is a peptide chain that (i) has a minimum of three amino acid residues, (ii) has a maximum of about fifty amino acid residues, and (iii) binds a heparin-binding growth factor receptor (HBGFR);

$R_1$ is a single trifunctional amino acid residue covalently bonded to each X;

Each $R_2$ is independently a linker comprising a chain from 0 to about 20 backbone atoms including carbon, oxygen, sulfur, nitrogen and mixtures thereof covalently bonded to $R_1$ and X;

Each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative;

$R_4$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or $NH-R_3$;

Y is a linker comprising a chain from 0 to about 50 backbone atoms covalently bonded to $R_1$ and Z; and Z is a non-signaling peptide chain that includes a heparin binding domain, comprising an amino acid sequence that comprises (i) a minimum of one heparin binding motif, (ii) a maximum of about ten heparin binding motifs, and (iii) a maximum of about thirty amino acids.

Another aspect of the present invention provides that Y further comprises a linker that (i) is hydrophobic, (ii) comprises a chain of a minimum of about 9 and a maximum of about 50 atoms, and (iii) is not found in the natural ligand of the heparin-binding growth factor receptor (HBGFR) which X binds.

Another aspect of the present invention provides that the heparin-binding growth factor analog of formula I-IV has an avidity for heparin such that the synthetic heparin-binding growth factor analog binds heparin in 0.15 M NaCl, but is eluted by 1 M NaCl.

Another aspect of the present invention provides a heparin-binding growth factor analog of formula II:

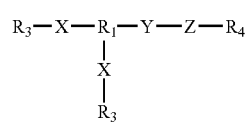

wherein $R_1$ is a diamine amino acid. All other features are as represented for formula I.

Another aspect of the present invention provides that the $R_1$ of the heparin-binding growth factor analog of formula II is an L- or D-diamine amino acid residue selected from the group consisting of 2,3 diamino propionyl amino acid, 2,4 diamino butylic amino acid, lysine and ornithine.

Another aspect of the present invention provides a heparin-binding growth factor analog of formula III:

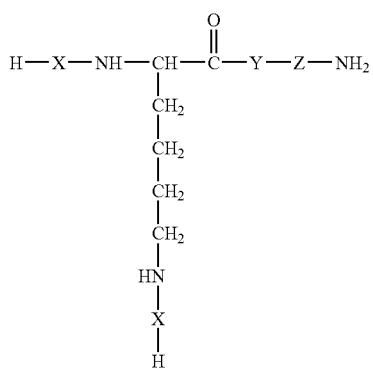

wherein:

C is carbon, H is hydrogen, N is nitrogen and O is oxygen. All other features are as represented for formula I.

Yet another aspect of the present invention provides a heparin-binding growth factor analog of of formula IV:

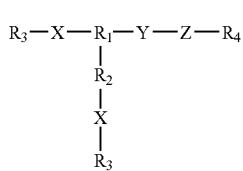

wherein:

$R_1$ is a trifunctional amino acid wherein the side chain of $R_1$ comprises a reactive sulfhydryl; and $R_2$ comprises a trifunctional amino acid wherein the side chain comprises a reactive sulfhydryl, wherein $R_2$ is covalently bonded to $R_1$ by a disulfide bond.

Another aspect of the present invention provides for a heparin-binding growth factor analog of formula III wherein $R_1$ and $R_2$ are each independently an L- or D-3-mercapto amino acid selected from the group consisting of L- or D-cysteine, L- or D-penicillamine, 3-mercapto phenylalanine, and a derivative of any of the foregoing.

Another aspect of the present invention provides for a heparin-binding growth factor analog of formula V:

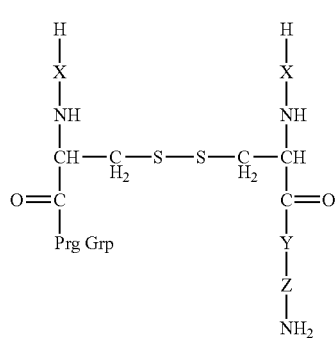

wherein:

Prg Grp is OH or a carboxy terminus protecting group; and
C is carbon, H is hydrogen, N is nitrogen, O is oxygen and S is sulfur. All other features are as represented for formula I.

Still another aspect of the present invention provides a heparin-binding growth factor analog of formula VI:

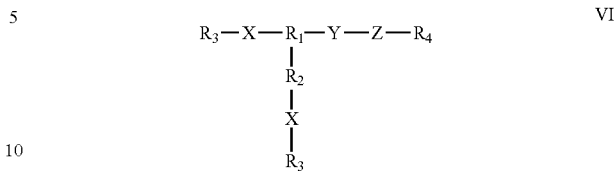

wherein:

$R_1$ is a trifunctional amino acid wherein the side chain comprises a first reactive group; and $R_2$ comprises a trifunctional amino acid wherein the side chain comprises a second reactive group, wherein $R_2$ is covalently bonded to $R_1$ by a covalent bond between the first reactive group and the second reactive group. All other features are as represented for formula I.

Yet another aspect of the present invention provides that X and Z of any of formulas I-VI are synthetic peptide chains.

Still another aspect of the present invention provides a heparin-binding growth factor analog comprising a synthetic peptide having two sequences branched from a single residue, the two sequences being the same and binding specifically to a heparin-binding growth factor receptor, and a sequence comprising a non-growth factor heparin-binding sequence covalently bonded to the single residue.

In another aspect, the single residue comprises a trifunctional amino acid residue.

In yet another aspect provides that the non-growth factor heparin-binding sequence is covalently bonded to the single residue by means of a linker.

N still another aspect provides a heparin-binding growth factor analog having a backbone chain from 2 to about 50 atoms.

In another aspect of the present invention, Y of any of formulas I-VI comprises between one and about thirty-three ethylene glycol units.

According to another aspect of the present invention, Y of any of formulas I-VI comprises a branched or unbranched, saturated or unsaturated alkyl chain of between one and about twenty carbon atoms.

In still another aspect of the present invention, Y of any of formulas I-VI comprises $[NH_2-(CH_2)_pCO]_q$ wherein p is from 1 to about 10 and q is from 1 to about 20.

In another aspect of the present invention, Y of any of formulas I-VI comprises a peptide sequence comprising from one to about 16 Gly residues.

Another aspect of the present invention, Z of any of formulas I-VI is BxBB or BBBxxB, wherein each B is independently lysine, arginine, ornithine, or histidine, and each x is a independently a naturally occurring amino acid.

In another aspect of the present invention, Z of any of formulas I-VI comprises at least two heparin-binding motifs.

In yet another aspect of the present invention, the covalent bonds between $R_1$ and Y of any of formulas I-VI comprise an amide, disulfide, thioether, Schiff base, reduced Schiff base, imide, secondary amine, carbonyl, urea, hydrazone or oxime bond.

In still another aspect of the present invention, covalent bonds between $R_1$ and each X of any of formulas I-VI comprise an amide, disulfide, thioether, Schiff base, reduced Schiff base, imide, secondary amine, carbonyl, urea, hydrazone or oxime bond.

In another aspect of the present invention the covalent bonds between Y and Z of any of formulas I-VI comprise an amide, disulfide, thioether, Schiff base, reduced Schiff base, imide, secondary amine, carbonyl, urea, hydrazone or oxime bond.

In another aspect of the present invention, X in any of formulas I-VI is any of SEQ ID NO:7 to SEQ ID NO:107, a portion thereof, a homolog thereof, or a homolog of a portion thereof, and Z comprises any of SEQ ID NO:1 to SEQ ID NO:6.

In yet another aspect of the present invention, the $R_2$ of any of formulas I-VI comprises between one and about three amino acid residues selected from the group consisting of glycine, a straight chain amino carboxylic acid, a bifunctional amino-PEG-acid spacer and combinations thereof.

In still another aspect of the present invention, Y of any of formulas I-VI comprises between one and about ten amino acid residues selected from the group consisting of glycine, a linear chain amino carboxylic acid, a bifunctional amino-PEG-acid spacer and combinations thereof.

In another aspect of the present invention, X of any of formulas I-VI comprises an amino acid sequence found in any of FGF-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, FGF-23, HBBM (heparin-binding brain mitogen), HB-GAF (heparin-binding growth associated factor), HB-EGF (heparin-binding EGF-like factor) HB-GAM (heparin-binding growth associated molecule, also known as pleiotrophin, PTN, HARP), TGF-α (transforming growth factor-α), TGF-βs (transforming growth factor-βs), VEGF (vascular endothelial growth factor), EGF (epidermal growth factor), IGF-1 (insulin-like growth factor-1), IGF-2 (insulin-like growth factor-2), PDGF (platelet derived growth factor), RANTES, SDF-1, secreted frizzled-related protein-1 (SFRP-1), small inducible cytokine A3 (SCYA3), inducible cytokine subfamily A member 20 (SCYA20), inducible cytokine subfamily B member 14 (SCYB14), inducible cytokine subfamily D member 1 (SCYD1), stromal cell-derived factor-1 (SDF-1), thrombospondins 1, 2, 3 and 4 (THBS1-4), platelet factor 4 (PF4), lens epithelium-derived growth factor (LEDGF), midikine (MK), macrophage inflammatory protein (MIP-1), moesin (MSN), hepatocyte growth factor (HGF, also called SF), placental growth factor, IL-1 (interleukin-1), IL-2 (interleukin-2), IL-3 (interleukin-3), IL-6 (interleukin-6), IL-7 (interleukin-7), IL-10 (interleukin-10), IL-12 (interleukin-12), IFN-α (interferon-α), IFN-γ (interferon-γ), TNF-α (tumor necrosis factor-α), SDGF (Schwannoma-derived growth factor), nerve growth factor, neurite growth-promoting factor 2 (NEGF2), neurotrophin, BMP-2 (bone morphogenic protein 2), OP-1 (osteogenic protein 1, also called BMP-7), keratinocyte growth factor (KGF), interferon-γ inducible protein-20, RANTES, and HIV-tat-transactivating factor, amphiregulin (AREG), angio-associated migratory cell protein (AAMP), angiostatin, betacellulin (BTC), connective tissue growth factor (CTGF), cysteine-rich angiogenic inducer 61 (CYCR61), endostatin, fractalkine/neuroactin, glial derived neurotrophic factor (GDNF), GRO2, hepatoma-derived growth factor (HDGF), and granulocyte-macrophage colony stimulating factor (GMCSF), or a homolog of an amino acid sequence found in any of the foregoing.

In yet another aspect of the present invention, a pharmaceutical composition comprises the heparin-binding growth factor analog of any of formulas I-VI or a pharmaceutically acceptable salt thereof and a pharmaceutical carrier.

Other aspects, objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

Additional objects and advantages of the present invention will be apparent in the following detailed description read in conjunction with the accompanying drawing figures.

DETAILED DESCRIPTION OF THE INVENTION

Figure 1:
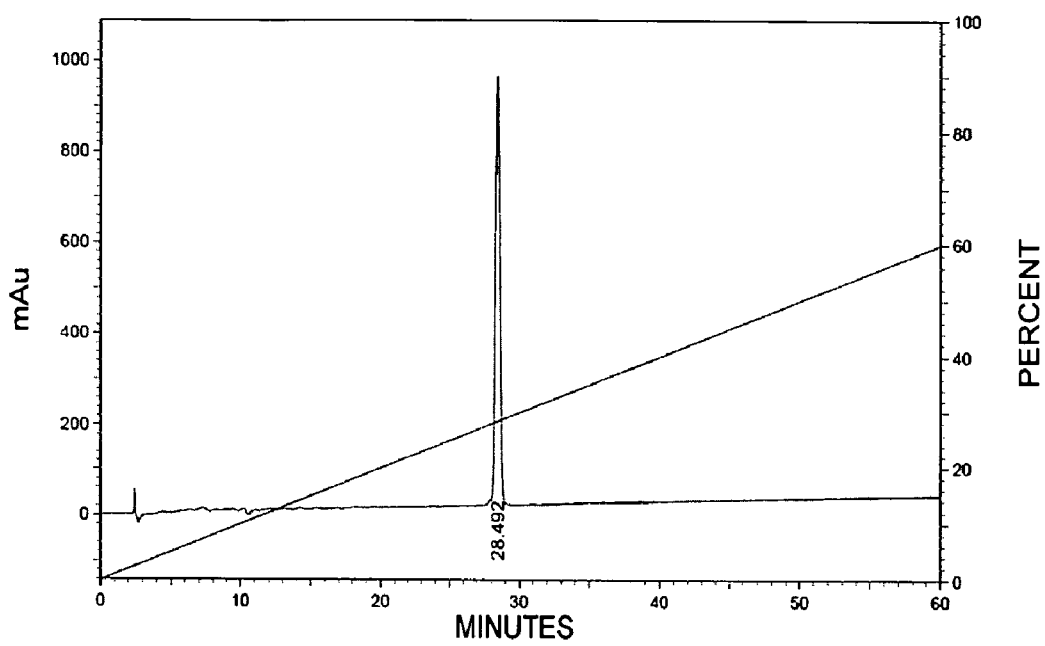
FIG. 1 illustrates an RP-HPLC profile for the SD1-1 analog according to one embodiment of the present invention.

Each synthetic HBGF analog of the invention contains two substantially similar sequences (homodimeric sequences) that are analogs of a particular HBGF that binds to a HBGFR, or alternatively that bind to a HBGFR without being an analog of any particular HBGF. The homodimeric sequences may be derived from any portion of a HBGF. The synthetic HBGF analog may be an analog of a hormone, a cytokine, a lymphokine, a chemokine or an interleukin, and may bind to any HBGFR for any of the foregoing.

One aspect of the present invention provides a synthetic HBGF analog of the present invention is a molecule of any one of formulas I to VI. HBGFs include any growth factor that binds selectively to heparin. For example, the HBGF can be any of the known FGFs (FGF-1 to FGF-23), Activin-A, HBBM (heparin-binding brain mitogen), HB-GAF (heparin-binding growth associated factor), HB-EGF (heparin-binding EGF-like factor) HB-GAM (heparin-binding growth associated molecule, also known as pleiotrophin, PTN, HARP), TGF-α (transforming growth factor-α), TGF-βs (transforming growth factor-βs), VEGF (vascular endothelial growth factor), EGF (epidermal growth factor), IGF-1 (insulin-like growth factor-1), IGF-2 (insulin-like growth factor-2), PDGF (platelet derived growth factor), RANTES, SDF-1, secreted frizzled-related protein-1 (SFRP-1), small inducible cytokine A3 (SCYA3), inducible cytokine subfamily A member 20 (SCYA20), inducible cytokine subfamily B member 14 (SCYB14), inducible cytokine subfamily D member 1 (SCYD1), stromal cell-derived factor-1 (SDF-1), thrombospondins 1, 2, 3 and 4 (THBS1-4), platelet factor 4 (PF4), lens epithelium-derived growth factor (LEDGF), midikine (MK), macrophage inflammatory protein (MIP-1), moesin (MSN), hepatocyte growth factor (HGF, also called SF), placental growth factor, IL-1 (interleukin-1), IL-2 (interleukin-2), IL-3 (interleukin-3), IL-6 (interleukin-6), IL-7 (interleukin-7), IL-10 (interleukin-10), IL-12 (interleukin-12), IFN-β, IFN-α (interferon-α), IFN-γ (interferon-γ), TNF-α (tumor necrosis factor-α), SDGF (Schwannoma-derived growth factor), nerve growth factor, neurite growth-promoting factor 2 (NEGF2), neurotrophin, BMP-2 (bone morphogenic protein 2), OP-1 (osteogenic protein 1, also called BMP-7), keratinocyte growth factor (KGF), interferon-γ inducible protein-20, RANTES, and HIV-tat-transactivating factor, amphiregulin (AREG), angio-associated migratory cell protein (AAMP), angiostatin, betacellulin (BTC), connective tissue growth factor (CTGF), cysteine-rich angiogenic inducer 61 (CYCR61), endostatin, fractalkine/neuroactin, or glial derived neurotrophic factor (GDNF), GRO2, hepatoma-derived growth factor (HDGF), granulocyte colony stimulating factor (G-CSF), granulocyte-macrophage colony stimulating factor (GMCSF), and the many growth factors, cytokines, interleukins and chemokines that have an affinity for heparin. It is also contemplated that agents of the invention can be modified through the introduction of appropriate binding sequences to direct analogs of growth factors, cytokines, interleukins, and chemokines, which do not normally bind to heparin, to have heparin-binding affinity.

The amino acid sequences of many of these and other HBGFs are available from the National Library of Medicine Protein Database at the internet site accessible through the world wide web address found at ncbi.nlm.nih.gov/entrez. These HBGF amino acid sequences on the foregoing internet site are hereby incorporated by reference. The use of synthetic HBGF analogs incorporating the amino acid sequences of the receptor binding domains from these and other HBGFs is specifically contemplated in the present invention.

In particular embodiments of the present invention, the synthetic HBGF analog of the present invention consists essentially of the molecule of any one of formulas I to VI, i.e. the molecule of any one of formula I to VI is the major active component in the synthetic HBGF analog composition.

The heparin-binding growth factors of formulas I to VI: The regions X and Z of the synthetic HBGF analogs of formulas I to VI include amino acid residues, and optionally the region Y includes amino acid residues. An amino acid residue is defined as —NHRCO—, where R can be hydrogen or any organic group. The amino acids can be D-amino acids or L-amino acids. Additionally, the amino acids can be α-amino acids, β-amino acids, γ-amino acids, or δ-amino acids and so on, depending on the length of the carbon chain of the amino acid.

The amino acids of the X, Y and Z component regions of the synthetic HBGF analogs of the invention can include any of the twenty amino acids found naturally in proteins, i.e. alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine, (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, Y and Z component regions of the synthetic HBGF analogs of the invention can include any of the naturally occurring amino acids not found naturally in proteins, e.g. β-alanine, betaine (N,N,N-trimethylglycine), homoserine, homocysteine, γ-amino butyric acid, ornithine, and citrulline.

Additionally, the amino acids of the X, Y and Z component regions of the synthetic HBGF analogs of the invention can include any of the non-biological amino acids, i.e. those not normally found in living systems, such as for instance, a straight chain amino carboxylic acid not found in nature. Examples of straight chain amino carboxylic acids include 6-aminohexanoic acid, 7-aminoheptanoic acid, 9-aminononanoic acid and the like.

In formula I, two X regions are covalently linked to $R_1$, either directly or through an $R_2$ group, where $R_1$ is a trifunctional amino acid residue, preferably a trifunctional alpha amino acid residue. It is to be appreciated that such covalent bonds may be to any chemically permitted functional group. Where the trifunctional amino acid residue is an amino acid with a reactive sulfhydryl side chain, such as cysteine, it is possible and contemplated that one X is covalently bonded through the N-terminus amine group, the second X is covalently bonded through the reactive sulfhydryl side chain, such as where $R_2$ includes a second cysteine residue covalently liked through a disulfide bond, and Y is covalently bonded to the second cysteine through the C-terminus carboxyl group thereof.

In a particularly preferred embodiment, $R_1$ is a diamine trifunctional amino acid residue, wherein $R_1$ is covalently bonded to Y through the carboxyl group of $R_1$, and the two X groups are covalently bonded to $R_1$ through the alpha amine and the epsilon amine of the side chain. Preferred groups for $R_1$ thus include 2,3 diamino propionyl amino acid, 2,4 diamino butylic amino acid, lysine or ornithine.

Particularly useful amino acid sequences as X regions of formulas I to VI include homologs of fragments of naturally occurring HBGFs that differ from the amino acid sequences of natural growth factor in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another amino acid of the same acidic or basic character.

In another alternative, the X regions of the synthetic HBGF analog can include an amino acid sequence that shows no detectable homology to the amino acid sequence of any HBGF. Peptides or growth factor analogs useful as components of the X region of the synthetic analogs of the present invention, that have little or no amino acid sequence homology with the cognate growth factor and yet bind HBGFRs may be obtained by any of a wide range of methods, including for instance, selection by phage display. See as an example: Sidhu et al. Phage display for selection of novel binding peptides. Methods Enzymol. 328:333-63 (2000).

The X region of the synthetic HBGF analogs of the invention can have any length that includes an amino acid sequence that effectively binds an HBGFR. Preferably, the X regions of the synthetic HBGF analogs have a minimum length of at least approximately three amino acid residues. More preferably, the X regions of the synthetic HBGF analogs have a minimum length of at least approximately six amino acid residues. Most preferably the X regions of the synthetic HBGF analogs have a minimum length of at least approximately ten amino acid residues. The X regions of the synthetic HBGF analogs of the invention preferably also have a maximum length of up to approximately fifty amino acid residues, more preferably a maximum length of up to approximately forty amino acid residues, and most preferably a maximum length of up to approximately thirty amino acid residues.

The $R_2$ regions of formulas I, IV or VI can include a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids). It is also contemplated that agents such as polyethylene glycol (PEG), polyethylene oxide (PEO), amino polyethylene glycol, bis-amine-PEG, and other variants of polyethylene glycol known to those skilled in the art can similarly be used.

The chain of atoms of the $R_2$ region of formulas I, IV or VI is covalently attached to X and $R_1$. The covalent bonds can be, for example, a peptide bond or other amide bond, or a thioether or ester bond. If present, the $R_2$ region preferably includes a chain of a minimum of about three backbone atoms. For example, where the covalent bonds are peptide bonds, the $R_2$ region may be formed from a chain of at least one, at least two or at least three amino acids. However, where other than peptide bonds are employed, the $R_2$ region may further include a cross-linking moiety. For example, where $R_1$ is Cys or another trifunctional amino acid with a reactive sulfhydryl, the $R_2$ region can be a linker consisting of a sulfhydryl reactive homo-bifunctional cross linker and a second Cys, or alternatively can include a hetero-bifunctional cross-linker, such as a cross-linker linking to the sulfhydryl on the $R_1$ side chain and carboxyl group of X.

In the synthetic HBGF analogs of the present invention, in one preferred embodiment the Y region of any of formulas I to VI is a linker that is sufficiently hydrophobic to non-covalently bind the HBGF analog to a polystyrene or polycaprolactone surface, or the like. In addition, the Y region may bind to other hydrophobic surfaces, particularly the hydrophobic surfaces formed from materials used in medical devices. Such surfaces are typically hydrophobic surfaces. Examples of suitable surfaces include but are not limited to those formed from hydrophobic polymers such as polycarbonate, polyester, polypropylene, polyethylene, polystyrene, polytetrafluoroethylene, expanded polytetrafluoroethylene, polyvinyl chloride, polyamide, polyacrylate, polyurethane, polyvinyl alcohol, polyurethane, poly ethyl vinyl acetate, poly(butyl methacrylate), poly(ethylene-co-vinyl acetate), polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steel, titanium, platinum, and nitinol. Preferably, the binding of the HBGF analogs to the hydrophobic surface is of sufficient quantity to be detected by an analytical method such as an enzyme-linked immunoassay or a biological assay.

According to one embodiment of the invention, the Y region of formulas I to VI includes a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non-natural amino acids, such as straight chain amino carboxylic acid; or a combination of any of the foregoing amino acids).

The chain of atoms of the Y region of formula I to VI is covalently attached to $R_1$ and to peptide Z. The covalent bonds can be, for example, peptide, amide, thioether or ester bonds. Preferably, the Y region includes a chain of a minimum of about nine backbone atoms. More preferably, the Y region includes a chain of a minimum of about twelve atoms. Most preferably, the Y region includes a chain of a minimum of about fifteen atoms. For example, the Y region may be formed from a chain of at least four, at least five or at least six amino acids. Alternatively, the Y region may be formed from a chain of at least one, at least two, or at least three aminohexanoic acid residues.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For example, the Y region may be formed from a chain of up to about twelve, up to about fifteen, or up to about seventeen amino acids.

The amino acid sequence of the Y region is preferably an artificial sequence, i.e. it does not include any amino acid sequence of four or more amino acid residues found in a natural ligand of a HBGF.

In a particular embodiment, the Y region includes a hydrophobic amino acid residue, or a chain of hydrophobic amino acid residues. The Y region can, for example, include one or more straight chain amino carboxylic acids, such as for example aminohexanoic acid residues, such as one, two, three or more aminohexanoic acid residues. Alternatively, the Y region can include up to about twelve, up to about fifteen, or up to about seventeen ethylene glycol residues. In another alternative embodiment, the Y region can include a combination of amino acid hydrophobic residues.

In another particular embodiment, the Y region of the molecule can include a branched or unbranched, saturated or unsaturated alkyl chain of between one and about twenty carbon atoms. In a further embodiment, the Y region can include a chain of hydrophilic residues, such as for instance, ethylene glycol residues. For instance, the Y region can include at least about three, or at least about four, or at least about five ethylene glycol residues.

The Z region of the molecule of formula I is a heparin-binding region and can include one or more heparin-binding motifs, BBxB or BBBxxB as described by Verrecchio et al. J. Biol. Chem. 275:7701 (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR] (SEQ ID NO:1), designating the first three amino acids as each independently selected from lysine or arginine, followed by any two amino acids and a sixth amino acid which is lysine or arginine.

The number of heparin binding motifs is variable. For instance, the Z region may include at least one, at least two, at least three or at least five heparin-binding motifs. Where there are more than one heparin-binding motifs, the motifs may be the same or different. Alternatively, the Z region includes up to a maximum of about ten heparin-binding motifs. In another alternative embodiment, the Z region includes at least four, at least six or at least eight amino acid residues. Further, in certain embodiments the Z region includes up to about twenty, up to about, twenty-five, or up to about thirty amino acid residues. It is to be realized that, in part, the avidity of the Z region for heparin is determined by the particular heparinbinding motifs selected and the number of such motifs in Z. Thus for particular applications both the selection and number of such motifs may be varied to provide optimal heparin binding of the Z region.

In a preferred embodiment, the amino acid sequence of the Z region is RKRKLERIAR (SEQ ID NO:2). In another embodiment, the amino acid sequence of the Z region is RKRKLGRIAR (SEQ ID NO:3). In yet another embodiment, the amino acid sequence of the Z region is RKRKLWRARA (SEQ ID NO:4). In yet another embodiment, the amino acid sequence of the Z region is RKRLDRIAR (SEQ ID NO:5), providing a heparin-binding motif derived from a modification of the sequence at residues 270-279 of the Jun/AP-1 DNA binding domain (Busch et al. Trans-Repressor Activity of Nuclear Glycosaminoglycans on Fos and Jun/AP-1 Oncoprotein-mediated Transcription. J. Cell Biol. 116:31-42, 1992). In yet another embodiment, the amino acid sequence of the Z region is RKRKLERIARC (SEQ ID NO:6). The presence of a terminal cysteine residue optionally affords the opportunity to link other molecules, including detection reagents such as fluorochromes, radioisotopes and other detectable markers, to the Z region, as well as the opportunity to link toxins, immunogens and the like.

Heparin-binding domains that bear little or no sequence homology to known heparin-binding domains are also contemplated in the present invention. As used herein the term "heparin-binding" means binding to the $-NHSO_3^-$ and sulfate modified polysaccharide, heparin, and also binding to the related modified polysaccharide, heparan. Such domains are contemplated to exhibit binding in physiological solutions including 0.15 M NaCl, and are expected to uncomplex at salt concentrations greater than 0.5 M NaCl.

The Z region of the synthetic HBGF analogs of the present invention confers the property of binding to heparin in low salt concentrations, up to about 0.15 M NaCl, optionally up to about 0.48 M NaCl, forming a complex between heparin and the Z region of the factor analog. The complex can be dissociated in 1 M NaCl to release the synthetic HBGF analog from the heparin complex.

The Z region is a non-signaling peptide. Accordingly, when used alone the Z region binds to heparin which can be bound to a receptor of a HBGF, but the binding of the Z region peptide alone does not initiate or block signaling by the receptor.

The C-terminus of the Z region may be blocked or free. For example, the C terminus of the Z region may be the free carboxyl group of the terminal amino acid, or alternatively, the C terminus of the Z region may be a blocked carboxyl group, such as for instance, an amide group.

Definitions: As used here and elsewhere, the following terms have the meanings given.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "amide" includes compounds that have a trivalent nitrogen attached to a carbonyl group (—$CO.NH_2$).

An "amine" includes compounds that contain an amino group (—$NH_2$).

A "diamine amino acid" is an amino acid or residue containing two reactive amine groups and a reactive carboxyl group. Representative examples include 2,3 diamino propionyl amino acid, 2,4 diamino butylic amino acid, lysine or ornithine.

The term "homologous", as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20% or 25% of the amino acid residues when the amino acid sequences of the two peptide homologs are aligned.

A "trifunctional amino acid" is an amino acid or residue with three reactive groups, one the N-terminus amine, a second the C-terminus carboxyl, and the third comprising all or a part of the side chain. Trifunctional amino acids thus include, by way of example only, diamine amino acids; amino acids with a reactive sulfhydryl group in the side chain, such as mercapto amino acids including cysteine, penicillamine, or 3-mercapto phenylalanine; amino acids with a reactive carboxyl group in the side chain, such as aspartic acid and glutamic acid; and amino acids with a reactive guanadium group in the side chain, such as arginine.

FGF Synthetic Analogs: In another particular aspect, the invention provides a synthetic FGF peptide analog. The synthetic FGF analogs represented by any of formulas I to VI above, wherein X is an FGF analog which can be any FGF, such as any of the known FGFs, including all 23 FGFs from FGF-1 to FGF-23.

The X region of the molecule of formulas I to VI can include an amino acid sequences found in an FGF, such as for instance FGF-2 or FGF-7. Alternatively, the X regions can include sequences not found in the natural ligand of the FGFR bound by the molecule.

The Y region of the synthetic FGF peptide analogs of any of formulas I to VI are not necessarily hydrophobic, and thus, if present, can be polar, basic, acidic, hydrophilic or hydrophobic. Thus, the amino acid residues of the Y region of synthetic FGF peptide analogs can include any amino acid, or polar, ionic, hydrophobic or hydrophilic group.

The X region of synthetic FGF peptide analogs can include an amino acid sequence that is 100% identical to an amino acid sequence found in a fibroblast growth factor or an amino acid sequence homologous to the amino acid sequence of a fibroblast growth factor. For instance, the X region can include an amino acid sequence that is at least about 50%, at least about 75%, or at least about 90% homologous to an amino acid sequence from a fibroblast growth factor. The fibroblast growth factor can be any fibroblast growth factor, including any of the known or yet to be identified fibroblast growth factors.

In a particular embodiment, the synthetic FGF analog of the invention is an agonist of the HBGFR. When bound to the HBGFR, the synthetic HBGF analog initiates a signal by the HBGFR.

In a further particular embodiment, the synthetic FGF analog of the invention is an antagonist of the HBGFR. When bound to the HBGFR, the synthetic HBGF analog blocks signaling by the HBGFR.

In another particular embodiment of the present invention, the synthetic FGF analog is an analog of FGF-2 (also known as basic FGF, or bFGF). In another particular embodiment of the present invention, the binding of the synthetic FGF analog to an FGF receptor initiates a signal by the FGF receptor. In a further particular embodiment, the binding of the synthetic FGF analog to the FGF receptor blocks signaling by the FGF receptor.

In a yet further particular embodiment, the present invention provides a synthetic FGF analog of FGF-2. In another particular embodiment, the present invention provides a synthetic FGF analog of FGF-2, wherein the amino acid sequence of the X region is YRSRKYTSWYVALKR (SEQ ID NO:7) from FGF-2. In yet another particular embodiment, the present invention provides a synthetic FGF analog wherein the amino acid sequence of the X region is NRFH-SWDCIKTWASDTFVLVCYDDGSEA (SEQ ID NO:8). In yet another embodiment, the present invention provides a synthetic FGF-2 analog wherein the amino acid sequence of the X region is HIKLQLQAEERGVVS (SEQ ID NO:9).

In a yet further particular embodiment, the invention provides a synthetic FGF analog of FGF-1, wherein the X region is YISKKHAEKNWFVGLKK (SEQ ID NO:10). This sequence is derived from amino acids bridging the beta 9 and beta 10 loop of FGF-1. In yet another particular embodiment, an FGF-1 analog is provided wherein the X region is HIQLQLSAESVGEVY (SEQ ID NO:11), corresponding to amino acids derived from the β-4 and β-5 region of FGF-1.

In a yet further particular embodiment, the invention provides a synthetic FGF analog of FGF-7, wherein the X region is YASAKWTHNGGEMFVALNQK (SEQ ID NO:12). In yet another embodiment of a synthetic FGF analog of FGF-7, the X region is the amino acid sequence YNIMEIRTVAVGIVA (SEQ ID NO:13).

Other FGF receptor binding domains, derived largely from targeting sequences in the C-terminus of human FGF, include the following sequences shown in Table 1:

TABLE 1

| CYTOKINE | PREFERRED X RECEPTOR BINDING DOMAIN | |
|---|---|---|
| FGF-10 | YASFNWQHNGRQMYVALNQK | (SEQ ID NO: 14) |
| FGF-22 | YASQRWRRRGQPNLALDRR | (SEQ ID NO: 15) |
| FGF-9 | YSSNLYKHVDTGRRYYVALNK | (SEQ ID NO: 16) |

TABLE 1-continued

| CYTOKINE | PREFERRED X RECEPTOR BINDING DOMAIN | |
|---|---|---|
| FGF-16 | YASTLYKHSDSERQYVALNK | (SEQ ID NO: 17) |
| FGF-20 | YSSNIYKHGDTGRRFVALNK | (SEQ ID NO: 18) |
| FGF-4 | YESYKYPGMFIALSKN | (SEQ ID NO: 19) |
| FGF-6 | YESDLYQGTYILSKYGR | (SEQ ID NO: 20) |
| FGF-12 | YSSTLYRQQESGRAWFLGNK | (SEQ ID NO: 21) |
| FGF-14 | YSSMLYRQQESGRAWFLGLNK | (SEQ ID NO: 22) |
| FGF-13 | YSSMIYRQQQSGRGWYLGLNK | (SEQ ID NO: 23) |
| FGF-11 | YASALYRQRRSGRAWYLDK | (SEQ ID NO: 24) |
| FGF-1 | SNGGHFLRIL | (SEQ ID NO: 65) |
| FGF-2 | KNGGFFLRIH | (SEQ ID NO: 66) |
| FGF-7 | RTQWYLRID | (SEQ ID NO: 67) |
| FGF-10 | FTKYFLKIE | (SEQ ID NO: 68) |
| FGF-22 | STHFFLRVD | (SEQ ID NO: 69) |
| FGF-9 | RTGFHLEIF | (SEQ ID NO: 70) |
| FGF-16 | RTGFHLEIF | (SEQ ID NO: 71) |
| FGF-20 | RTGFHLQIL | (SEQ ID NO: 72) |
| FGF-4 | NVGIGFHLQAL | (SEQ ID NO: 73) |
| FGF-6 | NVGIGFHLQVL | (SEQ ID NO: 74) |
| FGF-12 | QQGYFLQMH | (SEQ ID NO: 75) |
| FGF-14 | RQGYYLQMH | (SEQ ID NO: 76) |
| FGF-13 | RQGYHLQLQ | (SEQ ID NO: 77) |
| FGF-11 | RQGFYLQAN | (SEQ ID NO: 78) |
| FGF-8 | RTSGKHVQVL | (SEQ ID NO: 79) |
| FGF-17 | RTSGKHVQVT | (SEQ ID NO: 80) |
| FGF-18 | RTSGKHIQVL | (SEQ ID NO: 81) |
| FGF-3 | ATKYHLQLH | (SEQ ID NO: 82) |
| FGF-5 | RVGIGFHLQIY | (SEQ ID NO: 83) |
| FGF-19 | SGPHGLSSCFLRIR | (SEQ ID NO: 84) |
| FGF-21 | DDAQQTEAHLEIR | (SEQ ID NO: 85) |
| FGF-23 | ATARNSYHLQIH | (SEQ ID NO: 86) |

VEGF Synthetic Analogs: In another particular aspect, the invention provides a synthetic VEGF peptide analog. The synthetic VEGF analogs represented include, in one embodiment, a VEGF analog wherein the amino acid sequence of the X region is APMAEGGGQNHHEVVKFMDV (SEQ ID NO:25). In another embodiment, there is provided a synthetic VEGF peptide analog wherein the amino acid sequence of the X region is GATWLPPNPTK (SEQ ID NO:26). In yet another embodiment, there is provided a synthetic VEGF peptide analog wherein the amino acid sequence of the X region is NFLLSWVHWSLALLLYLHHA (SEQ ID NO:27).

BMP Synthetic Analogs: In another particular aspect, the invention provides a synthetic BMP peptide analog. The synthetic bone morphogenic protein analogs include embodiments wherein the X region includes the amino acid sequence LYVDFSDVGWNDW (SEQ ID NO:28), AISMLYLDENEKVVL (SEQ ID NO:29), ISMLYLDENEKVVLKNY (SEQ ID NO:30), EKVVLKNYQDMVVEG (SEQ ID NO:31), LVVKENEDLYLMSIAC (SEQ ID NO:32), AFYCHGECPFPLADHL (SEQ ID NO:33), PFPLADHLNSTNHAIVQTLVNSV (SEQ ID NO:34), TQLNAISVLYFDDSSNVILKKYRNMVV (SEQ ID NO:87), and/or HELYVSFRDLGWQDWIIAPEGYAAY (SEQ ID NO:88).

Alternatively, in another particular aspect the invention provides synthetic Avinin A, the synthetic Avinin A protein analogs include embodiments wherein the X region includes the amino acid sequence SMLYYDDGQNIIKK (SEQ ID NO:89), KKIINQGDDYYLMS (SEQ ID NO:90), and/or SMLYYDDGQNIIKKDI (SEQ ID NO:91).

Alternatively, in another particular aspect the invention provides synthetic G-CSF, the synthetic G-CSF protein analogs include embodiments wherein the X region includes the amino acid sequence ASSLPQSFLLKCLEQVRKIQ (SEQ ID NO:92), LDVADFATTIWQQMEEL (SEQ ID NO:93), and/or YKLAHPEELVL (SEQ ID NO:94).

Alternatively, in another particular aspect the invention provides synthetic GM-CSF, the synthetic GM-CSF protein analogs include embodiments wherein the X region includes the amino acid sequence WEHVNAIQEARRLLNL (SEQ ID NO:95), LQTRLELYKQGLRGSLTKLKGPLTMMASHYKQH (SEQ ID NO:96), and/or SFKENLKDFLLVI (SEQ ID NO:97).

Alternatively, in another particular aspect the invention provides synthetic IFN-beta, the synthetic IFN-beta protein analogs include embodiments wherein the X region includes the amino acid sequence SVQARWEAAFDLDLY (SEQ ID NO:98), YLDLDFAAEWRAQVS (SEQ ID NO:99), and/or SSSTGWNETIVENLI (SEQ ID NO:100).

Alternatively, in another particular aspect the invention provides synthetic PDGF, the synthetic PDGF protein analogs include embodiments wherein the X region includes the amino acid sequence KTRTEVFEISRRLIDRTNANFLVW (SEQ ID NO:101), and/or QVRKIEIVRKKPIFKK (SEQ ID NO:102).

Alternatively, in another particular aspect the invention provides synthetic SDF-1, the synthetic SDF-1 protein analogs include embodiments wherein the X region includes the amino acid sequence, KPVSLSYRCPCRFFESHVA (SEQ ID NO:103), and/or KWIQEYLEK (SEQ ID NO:104).

Alternatively, in another particular aspect the invention provides synthetic BMP, TGF and GDF (growth differentiation factor) peptide analogs as shown in Table 2 wherein the transforming growth factor family member peptides are particularly useful in augmenting the activity of endogenous or artificial BMP peptides or TGF peptides, wherein is shown (under the heading "preferred receptor binding domain") the sequence forming all or part of the X region of constructs of any of formulas I to VI.

TABLE 2

| CYTOKINE | PREFERRED X RECEPTOR BINDING DOMAIN | |
|---|---|---|
| TGF-β1 | IVYYVGRKPKVEQLSNMIVRS | (SEQ ID NO: 35) |
| TGF-β2 | TILYYIGKTPKIEQLSNMIVKS | (SEQ ID NO: 36) |
| TGF-β3 | LTILYYVGRTPKVEQLSNMVV | (SEQ ID NO: 37) |
| BMP-2 | AISMLYLDENEKVVLKNYQDMVV | (SEQ ID NO: 38) |

TABLE 2-continued

| CYTOKINE | PREFERRED X RECEPTOR BINDING DOMAIN | |
|---|---|---|
| BMP-3 | SSLSILFFDENKNVVLKVYPNMTV | (SEQ ID NO: 39) |
| BMP-3β | NSLGVLFLDENRNVVLKVYPNMSV | (SEQ ID NO: 40) |
| BMP-4 | AISMLYLDEYDKVVLKNYQEMVV | (SEQ ID NO: 41) |
| BMP-5 | AISVLYFDDSSNVILKKYRNMVV | (SEQ ID NO: 42) |
| BMP-6 | AISVLYFDDNSNVILKKYRNMVV | (SEQ ID NO: 43) |
| BMP-7 | AISVLYFDDSSNVILKKYRNMVV | (SEQ ID NO: 44) |
| BMP-8 | ATSVLYYDSSNNVILRKARNMVV | (SEQ ID NO: 45) |
| BMP-9 | ISVLYKDDMGVPTLKYHYEGMSV | (SEQ ID NO: 46) |
| BMP-10 | ISILYLDKGVVTYKFKYEGMAV | (SEQ ID NO: 47) |
| BMP-11 | INMLYFNDKQQIIYGKIPGMVV | (SEQ ID NO: 48) |
| BMP-12 | ISILYIDAANNVVYKQYEDMVV | (SEQ ID NO: 49) |
| BMP-13 | ISILYIDAGNNVVYKQYEDMVV | (SEQ ID NO: 50) |
| BMP-14 | ISILFIDSANNVVYKQYEDMVV | (SEQ ID NO: 51) |
| BMP-15 | ISVLMIEANGSILYKEYEGMIA | (SEQ ID NO: 52) |
| GDF-1 | ISVLFFDNSDNVVLRQYEDMVV | (SEQ ID NO: 53) |
| GDF-3 | ISMLYQDNNDNVILRHYEDMVV | (SEQ ID NO: 54) |
| GDF-8 | INMYLFNGKEQIIYGKIPAMVV | (SEQ ID NO: 55) |
| GDF-9 | LSVLTIEPDGSIAYKEYEDMIA | (SEQ ID NO: 56) |

It has surprisingly and advantageously been found that in the compounds of the present invention, including those of formulas I to VI, the X region may be synthesized in a reverse direction, such that considering the sequence AISMLYLDENEKVVL (SEQ ID NO:29) illustrated in the conventional N→C orientation, and using formula II, the first amino acid bound to either the $R_1$ side chain or N-terminus amine is the N-terminus amino acid residue (bound through its carboxyl group thereby forming a peptide bond), the second amino acid bound to the N-terminus amino acid residue is the 2 position residue, and so on, and the compounds nonetheless retain biological activity and specifically bind to a BMP receptor. It may be seen that such a construct has, based on a conventional N→C orientation, a reverse sequence, in that it is the carboxyl group of the conventional N-terminus amino acid residue that forms a peptide bond with an amine of $R_1$ where $R_1$ is a diamine amino acid. Thus again employing a conventional N→C orientation, the foregoing sequences may be employed in a reverse orientation, and the resulting compound of present invention is biologically active and may be employed as described herein. According to a preferred embodiment, the X region is the sequence LVVKENEDLYLMSIA (SEQ ID NO:57) (again considering the sequence in the conventional N→C orientation.

Other reverse sequences that may be employed, in whole or in part, including homologs thereto, in addition to LVVKENEDLYLMSIA (SEQ ID NO:57), include but are not limited to YNKLVVKENEDLYLMSI (SEQ ID NO:58), KKLIVNSSEDFYL (SEQ ID NO:59), WDNWGVDSFDVYL (SEQ ID NO:60), GEVVMDQYNKLVVKE (SEQ ID NO:61), LHDALPFPCEGHCYFA (SEQ ID NO:62), VSNVLTQVIAHNTSNLHDALPFP (SEQ ID NO:63), and LWKENEDLYLMSIAC (SEQ ID NO:64).

In certain embodiments of the invention, each of the $R_2$ regions of formula I are different, and in formulas IV and VI only one $R_1$ group is provided. Even in formula I it is contemplated that such regions may differ; for example, in formula I the $R_1$ may be a diamine amino acid, such as lysine. It is possible to utilize an orthogonal protecting group during synthesis to protect either the alpha amine or epsilon amine, to thereafter add one or amino acid residues or other groups to form an $R_2$ group, and then to remove the orthogonal protecting group, and proceed with parallel synthesis of the X groups from the deprotected amine on $R_1$ and the terminal amine on $R_2$.

Methods of synthesizing the heparin-binding growth factor analogs: The synthesis of the analogs of the invention can be achieved by any of a variety of chemical methods well known in the art. Such methods include bench scale solid phase synthesis and automated peptide synthesis in any one of the many commercially available peptide synthesizers. Preferably, the synthesizer has a per cycle coupling efficiency of greater than 99 percent.

The analogs of the present invention can be produced by stepwise synthesis or by synthesis of a series of fragments that can be coupled by similar well known techniques. See, for instance, Nyfeler, Peptide synthesis via fragment condensation. Methods Mol. Biol. 35:303-16 (1994); and Merrifield, Concept and early development of solid-phase peptide synthesis. Methods in Enzymol. 289:3-13 (1997). These methods are routinely used for the preparation of individual peptides. It is possible to assemble the analogs of the present invention in component parts, such as peptides constituting the X, Y and Z components thereof, and to thereafter couple such component parts to assemble the analog. See, for instance, Dawson and Kent, Synthesis of native proteins by chemical ligation. Annu. Rev. Biochem. 69:923-960 (2000); and Eom et al., Tandem ligation of multipartite peptides with cell-permeable activity. J. Am. Chem. Soc. 125:73-82 2003). However, in a preferred embodiment the compounds of the present invention are synthesized by solid phase synthesis, with the C-terminus residue of the Z region of formulas I to VI bound to resin, and the synthesis proceeding stepwise. Conventional protecting groups are employed as required, with deprotection either prior to, during or following cleavage of the peptide from the resin. By way of example only, for compounds of the present invention containing one or more lysine residues in addition to that at the $R_1$ position of formula I, such additional lysine residues will conventionally be protected with a protecting group, and deprotected following synthesis.

Peptide libraries that can be used to screen for a desired property, such as binding to an HBGFR, can be prepared by adaptations of these methods. See for instance, Fox, Multiple peptide synthesis, Mol. Biotechnol. 3:249-58 (1995); and Wade and Tregear, Solid phase peptide synthesis: recent advances and applications. Austral. Biotechnol. 3:332-6 (1993).

In a particular embodiment, the synthetic HBGF analog of the invention is an agonist of the HBGFR. When bound to the HBGFR, the synthetic HBGF analog initiates a signal by the HBGFR.

In another particular embodiment, the synthetic HBGF analog of the invention is an antagonist of the HBGFR. When bound to the HBGFR, the synthetic HBGF analog blocks signaling by the HBGFR.

In a particular aspect, the invention provides a method for stimulating growth factor receptor signaling in a cell by contacting the cell with an effective amount of a synthetic HBGF analog according to formulas I to VI. The effective amount can be readily determined by one of skill in the art. The signaling can result in cytokine release from the cell, stimulation or inhibition of proliferation or differentiation of the cell, chemotaxis of the cell, stimulation or inhibition of the immune system of the mammal.

Methods of use of the HBGFs of the invention: The HBGF analogs of the invention provide a cost effective and potentially unlimited source of biologically active molecules that are useful in a number of ways, including as soluble prophylactic or therapeutic pharmaceutical agents, such as for instance for administration as a soluble drug for prevention or treatment of various diseases, including for example, uses in cancer therapy and radioprotection.

The synthetic HBGF analogs of present invention are also useful as biologically active agents for coating of medical devices, such as for instance, sutures, implants and medical instruments to promote biological responses, for instance, to stimulate growth and proliferation of cells, or healing of wounds.

In one aspect, the present invention provides a method and compositions for treating a mammal that has been exposed to a harmful dose of radiation. The method includes administering an effective dose of a synthetic HBGF analog of the invention which is an FGF analog to the mammal. The treatment is particularly useful in the prevention or treatment of mucositis, gastrointestinal syndrome (G.I. syndrome), or radionecrosis such as can result from exposure to radiation. The HBGF analog can be administered parenterally, orally, or topically. Alternatively, the HBGF analog can be delivered loco-regionally, e.g. on an analog coated medical device. In a related embodiment, the present invention provides a method for treating a mammal that has been administered a dose of a chemotherapeutic agent, to ameliorate the toxicity of the chemotherapeutic agent to the mammal. In a particular embodiment of the above-described methods, the mammal is a human. In another particular embodiment of the method, the HBGF analog is an FGF-2 analog or an FGF-7 analog.

In another aspect, the invention provides a method and compositions for treating a mammal with bone injury, by providing a HBGF analog of the present invention having an X region reactive with a BMP HBGFR, such as an analog of BMP-2. For example, such HBGF analogs of the present invention may be administered as a pharmaceutical agent, or may be employed as an additive to bone matrix or bone graft materials.

In another aspect, the invention provides a method and compositions for preparation of cell or organ implant sites. In one embodiment, a homodimeric HBGF analog of FGF-2 of the present invention is administered by a percutaneous route to stimulate localized angiogenesis prior to implant of insulin-secreting pancreatic cells, and thereby improve the survival of the implanted cells. Similarly, a homodimeric HBGF analog of FGF-2 of the present invention is administered into ischemic heart tissue prior to the implant of myocte stem cells.

In another aspect, the invention provides a method and compositions to increase cellular attachment to and cellular retention on blood-contacting surfaces of medical devices. In one embodiment, a homodimeric HBGF analog of VEGF of the present invention is applied on vascular graft materials such that the bound analog recruits and binds circulating endothelial stem cells from the blood, thereby resulting in endothelialization of the graft surface with resultant long-term thromboresistance being imparted to the graft.

In another aspect, the invention provides a method and compositions to increase and provide for membrane-guided tissue growth.

In another aspect, the invention provides a method and composition for treatment of difficult-to-treat dermal wounds, including ulcers. In one embodiment, a homodimeric HBGF analog of TGF-β1 is applied topically in a pharmaceutically acceptable cream or gel for treatment of ulcerated bed sores and similar difficult-to-treat dermal wounds.

In yet another aspect, the invention provides a method and compositions to selectively increase cellular populations in vitro. For example, a homodimeric HBGF analog of TGF-β1 is formulated in a tissue culture medium to specifically stimulate the growth of chondrocytes, stem cells which give rise to chondrocytes, or pluripotent cells which give rise of chondrocytes. Similarly, a homodimeric HBGF analog of VEGF may be employed to stimulate the growth of endothelial cells.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, aneurysm coils, embolization particles, microbeads, dental implants, bone prostheses, tissue scaffolds, artificial joints or a controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al. in U.S. Pat. No. 6,342,591 teach an amphipathic coating for medical devices for modulating cellular adhesion composition, and is incorporated herein by reference.

In one embodiment, the invention provides a method for delivering an active peptide to a mammal, the method includes (i) providing a medical device coated on its surface with a synthetic HBGF analog of formulas I to VI, the synthetic HBGF analog being bound to the surface of the medical device by non-covalent bonds; and (ii) placing the medical device onto a surface of, or implanting the medical device into, the mammal.

In a particular embodiment of the above method, the non-covalent bonds are associations between the heparin binding domain of the synthetic HBGF analog and a heparin-containing compound bound to the surface of the medical device. The heparin-containing compound bound to the surface of the medical device can be any heparin-containing compound, such as for instance, benzyl-bis(dimethylsilylmethyl)oxy carbamoyl-heparin.

In another particular embodiment of the above method, the medical device is not pre-coated with a heparin-containing compound before being coated with the synthetic HBGF analog of formulas I to VI.

Heparin-Binding Growth Factor Analog Pharmaceutical Applications: The HBGF analogs of this invention can be used for as an active ingredient in pharmaceutical compositions for both medical applications and animal husbandry or veterinary applications. Typically, the HBGF analog or pharmaceutical composition is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The HBGF analogs of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the HBGF analog of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the HBGF analogs of this invention are prepared in a suitable solvent for the HBGF analog and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the HBGF analogs of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a HBGF analog of this invention and a pharmaceutically acceptable carrier. The carrier may be a liquid formulation, and in one embodiment a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Thus the HBGF analog compositions of this invention may be formulated or compounded into pharmaceutical compositions that include at least one HBGF analog of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, PEG, PEO, mannitol, sodium chloride or sodium citrate, as well as any number of simple sugars, including sucrose, dextrose, lactose and the like, and combinations of the foregoing. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a HBGF analog of this invention over a period of time.

In practical use, the HBGF analogs of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

If the HBGF analog pharmaceutical composition is administered by injection, the injection may be intravenous, subcutaneous, intramuscular, intraperitoneal or other means known in the art. The HBGF analogs of this invention may alternatively be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the HBGF analogs of invention are introduced across an epidermal layer of cells may be employed. Administration means may thus include administration through mucous membranes, buccal administration, oral administration, dermal administration, inhalation administration, nasal administration, urethral administration, vaginal administration, and the like.

In general, the actual quantity of HBGF analog of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect.

Heparin-binding growth factors: The fibroblast growth factors, FGFs, constitute a family of related proteins controlling normal growth and differentiation of mesenchymal, epithelial, and neuroectodermal cell types. Homologs have been found in a wide variety of species. FGFs show a very high affinity to heparin and are therefore also referred to as heparin-binding growth factors (HBGFs). As used herein, the term HBGFs includes all FGFs.

Two main types of FGF are known. The first type of FGF was isolated initially from brain tissue. It was identified by its proliferation-enhancing activities for murine fibroblasts, such as 3T3 cells. Due to its basic pI the factor was named basic FGF (bFGF, or HBGF-2, heparin-binding growth factor-2) and is now generally referred to as FGF-2. This is the prototype of the FGF family.

Another type of FGF, also initially isolated from brain tissues, is acidic FGF (aFGF, also known as HBGF-1, heparin-binding growth factor-1 or HBGF-α, heparin-binding growth factor-α), now generally referred to as FGF-1. It was identified by its proliferation-enhancing activity for myoblasts.

Other fibroblast growth factors belonging to the same family include FGF-3 (or HBGF-3, heparin-binding growth factor-3, originally called int-2; see Fekete, Trends in Neurosci. 23:332 (2000)), FGF-4 (HBGF-4, heparin-binding growth factor-4, initially recognized as the product of the oncogene hst; see Sakamoto et al., Proc. Natl. Acad. Sci. USA 91:12368-72), and FGF-5 (originally called HBGF-5, see Bates et al. Biosynthesis of human fibroblast growth factor 5. Mol. Cell. Biol. 11:1840-1845 (1991)); Burgess and Maciag, The heparin-binding (fibroblast) growth factor family of proteins. Ann. Rev. Biochem. 58: 575-606 (1989); and Zhan et al. The human FGF-5 oncogene encodes a novel protein related to fibroblast growth factors. Mol. Cell. Biol. 8:3487-3495 (1988)).

FGF-6 is also known as HBGF-6, and sometimes called hst-2 or oncogene hst-1 related growth factor, see Iida et al. Human hst-2 (FGF-6) oncogene: cDNA cloning and characterization. Oncogene 7:303-9 (1992); and Marics et al. Characterization of the HST-related FGF-6 gene, a new member of the fibroblast growth factor gene family. Oncogene 4:335-40 (1989).

FGF-7 or K-FGF is also known as KGF or keratinocyte growth factor (See Aaronson et al. Keratinocyte growth factor. A fibroblast growth factor family member with unusual target cell specificity. Annals NY Acad. Sci. 638:62-77 (1991)); Finch et al. Human KGF is FGF-related with properties of a paracrine effector of epithelial cell growth. Science 245:752-5 (1989); Marchese et al. Human keratinocyte growth factor activity on proliferation and differentiation of human keratinocytes: differentiation response distinguishes KGF from EGF family. J. Cellular Physiol. 144: 326-32 (1990)).

FGF-8 was found to be identical to androgen-induced growth factor, AIGF and has been well studied (See Blunt et al. Overlapping expression and redundant activation of mesenchymal fibroblast growth factor (FGF) receptors by alternatively spliced FGF-8 ligands. J. Biol. Chem. 272:3733-8 (1997)); Dubrulle et al. FGF signaling controls somite boundary position and regulates segmentation clock control of spatiotemporal Hox gene activation. Cell 106:219-232 (2001); Gemel et al. Structure and sequence of human FGF8. Genomics 35:253-257 (1996); Tanaka et al. A novel isoform of human fibroblast growth factor 8 is induced by androgens and associated with progression of esophageal carcinoma. Dig. Dis. Sci. 46:1016-21 (2001)).

FGF-9 was originally called glia activating factor, or HBGF-9. See Miyamoto et al. Molecular cloning of a novel cytokine cDNA encoding the ninth member of the fibroblast growth factor family, which has a unique secretion pattern. Mol. Cell. Biol. 13:4251-9 (1993); and Naruo et al. Novel secretory heparin-binding factors from human glioma cells (glia-activating factors) involved in glial cell growth. J. Biol. Chem. 268: 2857-64 (1993).

FGF-10 is also called KGF-2, keratinocyte growth factor-2 (see Kok et al. Cloning and characterization of a cDNA encoding a novel fibroblast growth factor preferentially expressed in human heart. Biochem. Biophys. Res. Comm. 255:717-721, (1999)).

Several FGF-related factors have been described as fibroblast growth factor homologous factors (FHFs) and are also referred to as FGF-11 (FHF-3), FGF-12 (FHF-1), FGF-13 (FHF-2, see Greene et al. Identification and characterization of a novel member of the fibroblast growth factor family. Eur. J. Neurosci. 10:1911-1925 (1998)), and FGF-14 (FHF-4).

FGF-15 is expressed in the developing nervous system and was identified as a gene regulated by transcription factor E2A-Pbx1. McWhirter et al. A novel fibroblast growth factor gene expressed in the developing nervous system is a downstream target of the chimeric homeodomain oncoprotein E2A-Pbx1. Development 124:3221-3232 (1997).

FGF-16 was isolated as a cDNA clone from rat heart by homology-based polymerase chain reaction expressing an FGF of 207 amino acids. FGF-16 is 73% identical to FGF-9. Miyake et al. Structure and expression of a novel member, FGF-16, of the fibroblast growth factor family. Biochem. Biophys. Res. Commun. 243:148-152 (1998).

The cDNA encoding FGF-17 was isolated from rat embryos and encodes a protein of 216 amino acids. When expressed in 3T3 fibroblasts, mouse FGF-17 is transforming. During embryogenesis, FGF-17 is expressed at specific sites in forebrain, the midbrain-hindbrain junction, the developing skeleton and in developing arteries. See Hoshikawa et al. Structure and expression of a novel fibroblast growth factor, FGF-17, preferentially expressed in the embryonic brain. Biochem. Biophys. Res. Commun. 244:187-191 (1998); and Xu et al. Genomic structure, mapping, activity and expression of fibroblast growth factor 17. Mechanisms of Development 83:165-178 (1999).

The cDNA encoding FGF-18 was isolated from rat embryos encoding a protein of 207 amino acids. FGF-18 is a glycosylated protein and is most similar to FGF-8 and FGF-17. Injection of recombinant murine FGF-18 has been shown to induce proliferation in tissues of both epithelial and mesenchymal origin, particularly in liver and small intestine. Recombinant rat FGF-18 induces neurite outgrowth in PC12 cells. Recombinant murine FGF-18 protein stimulates proliferation in NIH 3T3 fibroblasts in vitro in a heparan sulfate-dependent manner. For general information see Hu et al. FGF-18, a novel member of the fibroblast growth factor family, stimulates hepatic and intestinal proliferation. Mol. Cell. Biol. 18:6063-6074 (1998); and Ohbayashi et al. Structure and expression of the mRNA encoding a novel fibroblast growth factor, FGF-18. J. Biol. Chem. 273:18161-18164 (1998).

FGF-19 is related distantly to other members of the FGF family. FGF-19 mRNA is expressed in several tissues including fetal cartilage, skin, and retina, as well as adult gall bladder. It is overexpressed in a colon adenocarcinoma cell line. FGF-19 is a high affinity, heparin-dependent ligand for the FGF-4 receptor. See Xie et al. FGF-19, a novel fibroblast growth factor with unique specificity for FGFR4 Cytokine 11:729-735 (1999).

FGF-20 is expressed in normal brain, particularly the cerebellum, and in some cancer cell lines. FGF-20 mRNA is expressed preferentially in the substantia nigra pars compacta. Recombinant FGF-20 protein induces DNA synthesis in a variety of cell types and is recognized by multiple FGF receptors. FGF-20 functions like an oncogene, causing a transformed phenotype when expressed in the 3T3 fibroblast cell line. These transformed cells are tumorigenic in nude mice. See Jeffers et al. Identification of a novel human fibroblast growth factor and characterization of its role in oncogenesis. Cancer Res. 61:3131-8 (2001); and Ohmachi et al. FGF-20, a novel neurotrophic factor, preferentially expressed in the substantia nigra pars compacta of rat brain. Biochem. Biophys. Res. Commun. 277:355-60 (2000).

FGF-21 was isolated from mouse embryos. FGF-21mRNA is most abundant in the liver with lower levels in the thymus. FGF-21 is most similar to human FGF-19. See Nishimura et al. Identification of a novel FGF, FGF-21, preferentially expressed in the liver. Biochim. Biophys. Acta 1492:203-6 (2000).

The cDNA encoding FGF-22 (170 amino acids) was isolated from human placenta. FGF-22 is most similar to FGF-10 and FGF-7. Murine FGF-22 mRNA is expressed preferentially in the skin. FGF-22 mRNA in the skin is found preferentially in the inner root sheath of the hair follicle. See Nakatake et al. Identification of a novel fibroblast growth factor, FGF-22, preferentially expressed in the inner root sheath of the hair follicle. Biochim. Biophys. Acta 1517: 460-3 (2001).

FGF-23 is most similar to FGF-21 and FGF-19. The human FGF-23 gene maps to chromosome 12p13 linked to human FGF-6 gene. FGF-23 mRNA is expressed mainly in the brain (preferentially in the ventrolateral thalamic nucleus) and thymus at low levels. Missense mutations in the FGF-23 gene have been found in patients with autosomal dominant hypophosphataemic rickets. Overproduction of FGF23 causes tumor-induced osteomalacia, a paraneoplastic disease characterized by hypophosphatemia caused by renal phosphate wasting. See Yamashita et al. Identification of a novel fibroblast growth factor, FGF-23, preferentially expressed in the ventrolateral thalamic nucleus of the brain. Biochem. Biophys. Res. Commun. 277:494-8 (2000); and Shimada et al. Cloning and characterization of FGF23 as a causative factor of tumor-induced osteomalacia. Proc. Natl. Acad. Sci. (USA) 98:6500-5 (2001).

HBBM (Heparin-binding brain mitogen) was isolated initially as a heparin binding protein from brain tissues of several species and is identical to heparin-binding neurite promoting factor. See Huber et al. Amino-terminal sequences of a novel heparin-binding protein with mitogenic activity for endothelial cells from human bovine, rat, and chick brain: high interspecies homology. Neurochem. Res. 15:435-439 (1990).

HB-GAF (heparin-binding growth associated factor) is a neurotrophic and mitogenic factor identical to HBNF (heparin-binding neurite-promoting factor). See Kuo et al. Characterization of heparin-binding growth-associated factor receptor in NIH 3T3 cells. Biochem. Biophys. Res. Commun. 182:188-194 (1992).

HB-EGF (heparin-binding EGF-like factor) is found in conditioned media of cell line U937 and is also synthesized by macrophages and human vascular smooth muscle cells. HB-EGF is a monomeric heparin-binding O-glycosylated protein of 86 amino acids and is processed from a precursor of 208 amino acids. Several truncated forms of HB-EGF have been described. HB-EGF is a potent mitogen for NIH 3T3 cells, keratinocytes and smooth muscle cells, but not for endothelial cells. The mitogenic activity on smooth muscle cells is much stronger than for EGF and appears to involve interactions with cell surface heparan sulfate proteoglycans. HB-EGF is a major growth factor component of wound fluid and may play an important role in wound healing. See Abraham et al. Heparin-binding EGF-like growth factor: characterization of rat and mouse cDNA clones, protein domain conservation across species, and transcript expression in tissues. Biochem. Biophys. Res. Commun. 190:125-133 (1993); Higashiyama et al. A heparin-binding growth factor secreted by macrophage like cells that is related to EGF. Science 251:936-9 (1991); and Marikovsky et al. Appearance of heparin-binding EGF-like growth factor in wound fluid as a response to injury. Proc. Natl. Acad. Sci. (USA) 90:3889-93.

HB-GAM (heparin-binding growth associated molecule) also referred to as HBNF (heparin-binding neurite promoting factor) is a protein of 15.3 kDa isolated as a heparin binding protein from brain tissues of several species. HB-GAM promotes growth of SW-13 cells in soft agar. Courty et al. Mitogenic properties of a new endothelial cell growth factor related to pleiotrophin. Biochem. Biophys. Res. Commun. 180: 145-151 (1991); and Hampton et al. Structural and functional characterization of full-length heparin-binding growth associated molecule. Mol. Biol. Cell. 3:85-93 (1992).

TGF-beta (TGF-β) exists in at least five isoforms, known TGF-β1, TGF-β2, TGF-β3, TGF-β4 and TGF-β5, that are not related to TGF-α. Their amino acid sequences display homologies on the order of 70-80 percent. TGF-β1 is the prevalent form and is found almost ubiquitously while the other isoforms are expressed in a more limited spectrum of cells and tissues.

TGF-beta is the prototype of a family of proteins known as the TGF-beta superfamily. This family includes inhibins, Activin A, MIS (Mullerian activating substance) and BMPs (Bone morphogenic proteins). Burt, Evolutionary grouping of the transforming growth factor-beta superfamily. Biochem. Biophys. Res. Commun. 184:590-5 (1992).

EXAMPLES

Example 1

A compound of the present invention was synthesized by solid phase peptide chemistry with the general structure of formula I wherein X is a BMP-2 receptor binding amino acid sequence having the sequence AISMLYLDEKVVL(SEQ ID NO:105) wherein the sequence was grown in parallel from the $R_1$ trifunctional amino acid of formula I when $R_2$ is 0 atoms and $R_1$ is lysine. The resulting synthetic growth modulator analog is of the following specific structure:

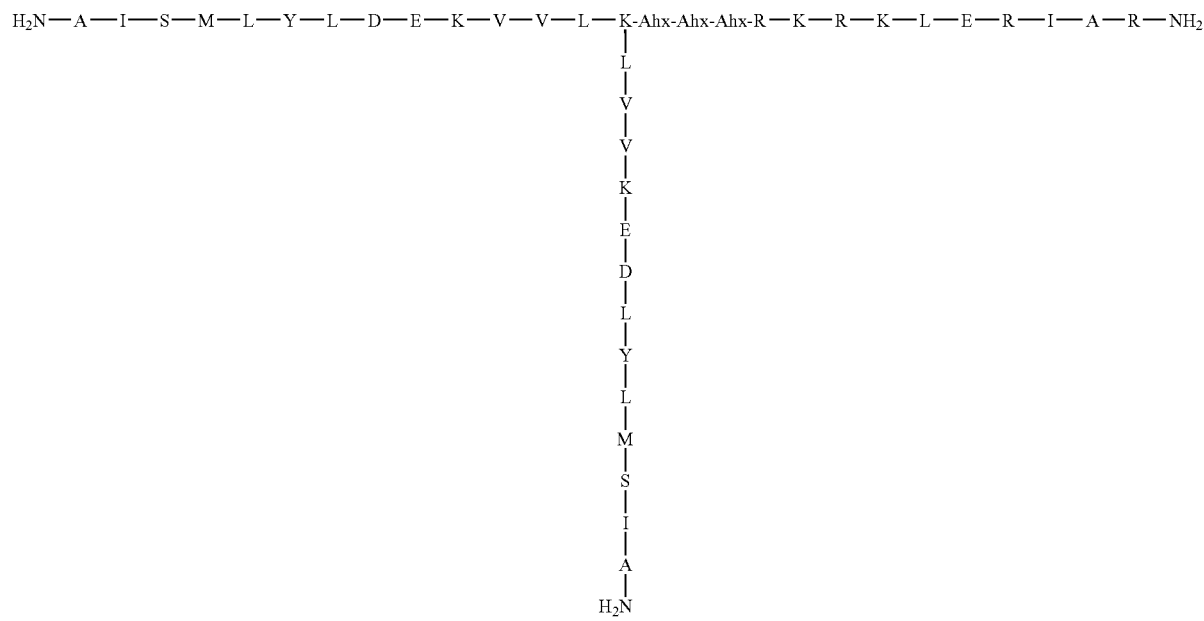

and is sometimes called B2A2-K-NS. In the foregoing structure, "Ahx" is 6-amino hexanoic acid, sometimes also called "6-Ahx" or "Hex". The single letters are standard amino acid single letter abbreviations for the naturally coded amino acids.

Example 2

A compound of the present invention was synthesized by solid phase peptide chemistry with the general structure of formula I wherein X is a BMP receptor binding amino acid sequence having the sequence LYFDESSNVILKK(SEQ ID NO:106) which was grown in parallel from the trifunctional amino acid of formula I when $R_2$ is 0 atoms and $R_1$ is a lysine. The resulting synthetic growth modulator analog is of the following specific structure:

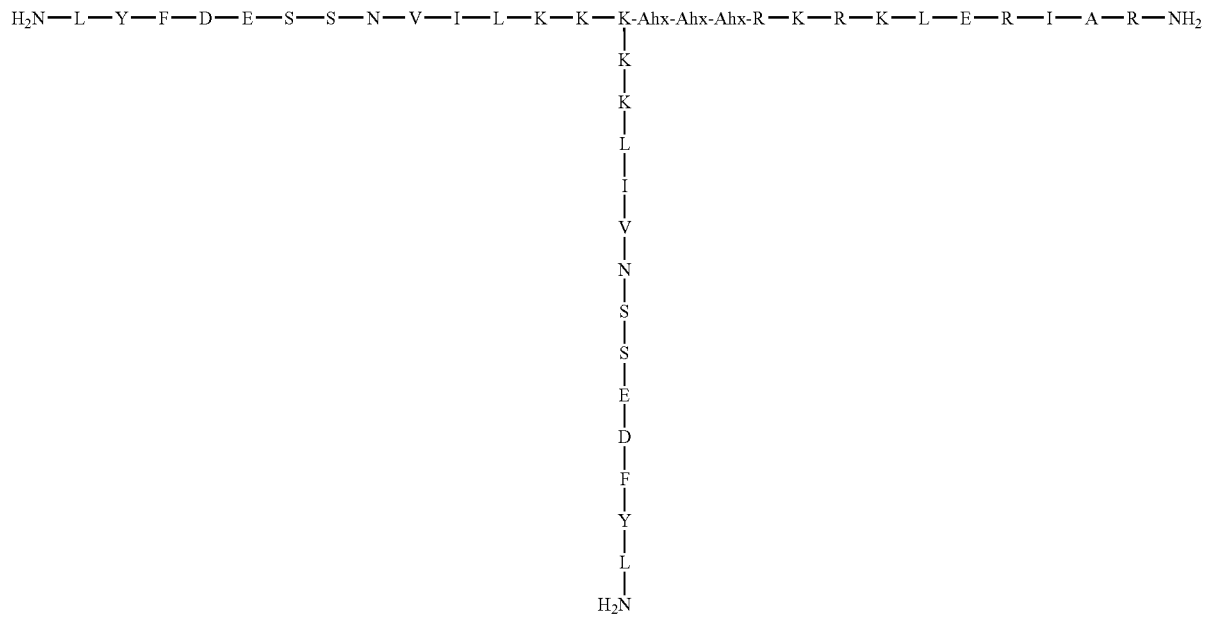

and is sometimes called B7A1-K-NS. In the foregoing structure, "Ahx" is 6-amino hexanoic acid, sometimes also called "6-Ahx" or "Hex". The single letters are standard amino acid single letter abbreviations for the naturally coded amino acids.

Example 3

A compound of the present invention is synthesized by solid phase peptide chemistry with the general structure of formula I wherein X is a BMP-2 receptor binding amino acid sequence having the sequence ISMLYLDENEKVVLKNY (SEQ ID NO:30) grown in parallel from an $R_1$ trifunctional amino acid of formula I and wherein $R_1$ is lysine. The resulting synthetic growth modulator analog is of the following specific structure:

NH₂—ISMLYLDENEKVVLKNYK-Ahx-Ahx-Ahx-RKRLDRIAR—NH₂
      |
      ISMLYLDENEKVVLKNY
      |
      NH₂

In the foregoing structure, "Ahx" is 6-amino hexanoic acid, sometimes also called "6-Ahx" or "Hex". The single letters are standard amino acid single letter abbreviations for the naturally coded amino acids.

Example 4

The synthetic FGF analog YRSRKYSSWYVALKRK(H-YRSRKYSSWYVALKR)-Ahx-Ahx-Ahx-RKRKLDRIAR-NH₂ was synthesized by standard solid phase peptide synthesis methods. In the compound YRSRKYSSWYVALKRK(H-YRSRKYSSWYVALKR)-Ahx-Ahx-Ahx-RKRKLDRIAR-NH₂, the $R_1$ group of formula I was a single trifunctional amino acid residue, here a diamine amino acid, lysine (K). The peptide of Example 4 has an estimated molecular weight of 5681.

The peptide of Example 4 was assembled stepwise by solid-phase synthesis on a substituted resin, using Fmoc chemistry for temporary protection of amino groups in the repetitive cycles. Protecting groups were used as required. Branching of the chain was accomplished by stepwise growth of identical chains from the alpha amino group and side-chain amino group of a single lysyl residue. The completed peptide chain was cleaved from the resin as C-terminal amides by acidolysis, which also removed the acid-labile side-chain protecting groups. The peptide of Example 4 was purified by reverse phase HPLC using a $C_{18}$ column in a continuous gradient elution of 0-60% B over 60 minutes, run at 1 mL/min, where A was 0.1% trifluoroacetate in water and B was 0.1% trifluoroacetate in acetonitrile. The general structure of the compound of Example 4 is shown below:

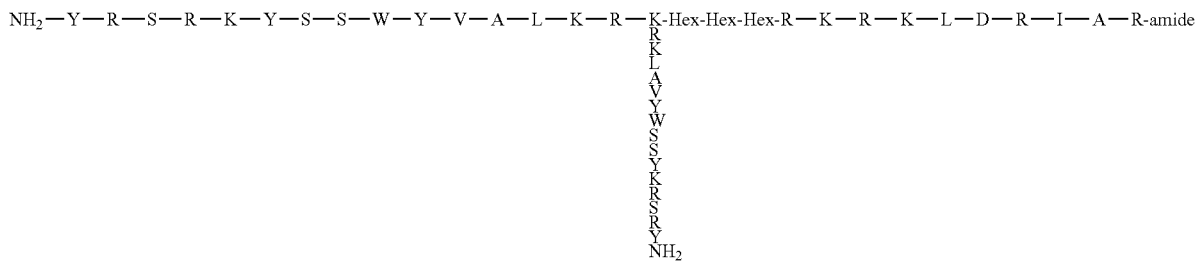

Example 5

Two peptides were synthesized as analogs of TGF as in Example 4, of the following structures:

```
T1A1-K-NS
H-PIVYYVGRKPKVEQK(H-PIVYYVGRKPKVEQ)-Ahx-Ahx-Ahx-
RKRKLERIAR-NH2

T1A2-K-NS
H-YIWSLDTQYSKVLK(H-YIWSLDTQYSKVL)-Ahx-Ahx-Ahx-
RKRKLERIAR-NH2
```

Example 6

A peptide was synthesized as a candidate agonist of PDGF-BB and designated PBA2-1C. The peptide was branched from a single lysine (K) at the $R_1$ position, where the N-terminus residue of the branched sequence CVRKIEIVRKK (SEQ ID NO:107) was a cysteine (C) residue. The resulting construct was a cyclic peptide, with the two X regions joined by a disulfide bond at the N-terminus cysteine.

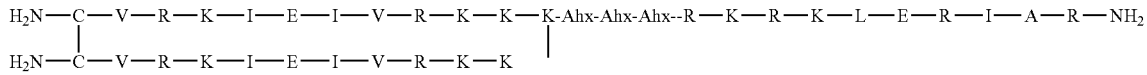

Figure 6:
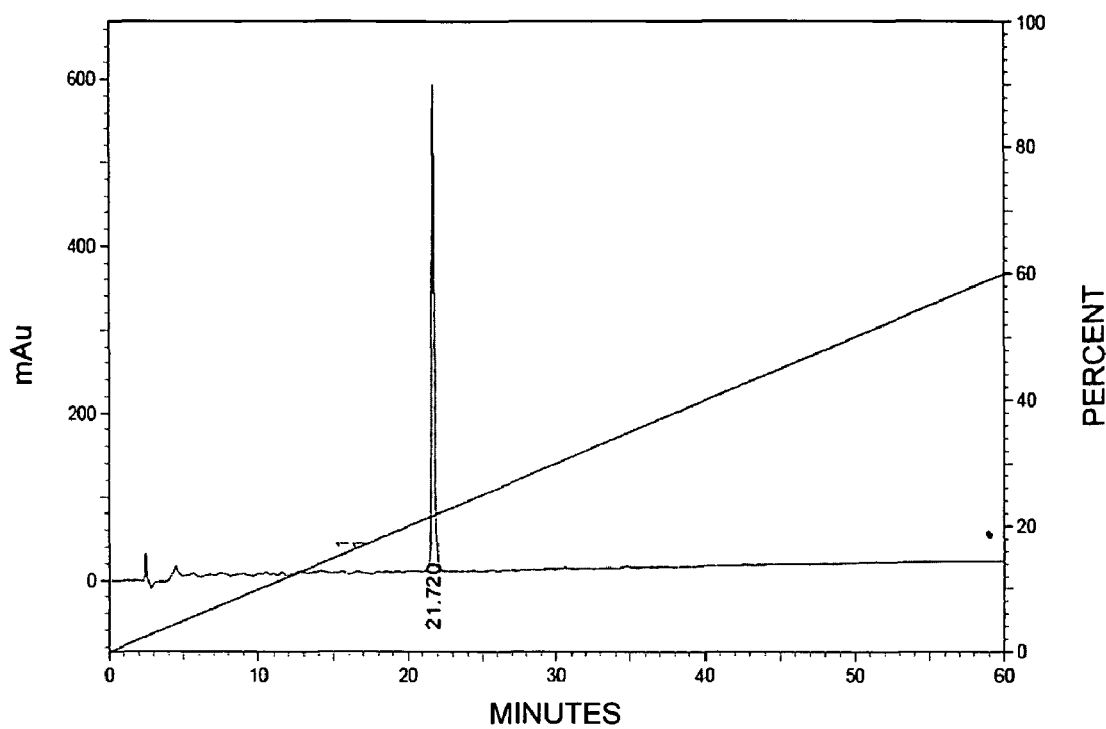
FIG. 6 illustrates analysis by RP-HPLC of PBA2-1C analog according to one embodiment of the present invention according to one embodiment of the present invention.

The peptide was was purified by RP-HPLC on a C18 column, using a linear gradient 0-60% acetonitrile/water (0.1% trifluoroacetic acid) run over 60 min at 1 ml/min flow rate (detection at 214 nm). The purified peptide generated a single uniform peak on analysis by RP-HPLC as indicated in FIG. 6.

Surface Plasmon Resonance (SPR) Analysis. Real-time biomolecular interactions were analyzed with a BIAcore 2000 system (Biacore Inc., Piscataway, N.J.). Soluble PDGF receptor, recombinant chimera of human PDGF-R-alpha and PSGF-R-beta (R &D Systems, Minneapolis, Minn.), was immobilized on research grade CM5 chips (Biacore Inc., Piscataway, N.J.). Following activation with EDC/NHS, the receptors were immobilized on activated CM5 chips. To obtain kinetic data, different concentrations of analytes in HBS-EP buffer were injected over the sensor chip at a flow rate of 50 μl/min. Peptide binding was measured in resonance units (RU). At the end of each sample injection (120 s) buffer was passed over the sensor surface to monitor the dissociation phase. Reference responses from blank flow cells were subtracted from receptor-containing flow cells for each analyte injection and the kinetic parameters for each interaction were determined by globally fitting the experimental data to a 1:1 interaction with BIAEVALUATION software (Biacore Inc., Piscataway, N.J.). The association rate constant and the dissociation rate constant ($k_a$ and $k_d$, respectively), and the equilibrium dissociation constant ($K_D$) are presented in the Table 3 for the receptors and PBA2-1.

TABLE 3

| PDGF R Alpha | | | PDGF R Beta | | |
|---|---|---|---|---|---|
| Ka | Kd | KD | Ka | Kd | KD |
| 1.98E+05 | 3.36E-03 | 1.70E-08 | 1.33E+05 | 2.96E-03 | 2.23E-08 |

Figure 7:
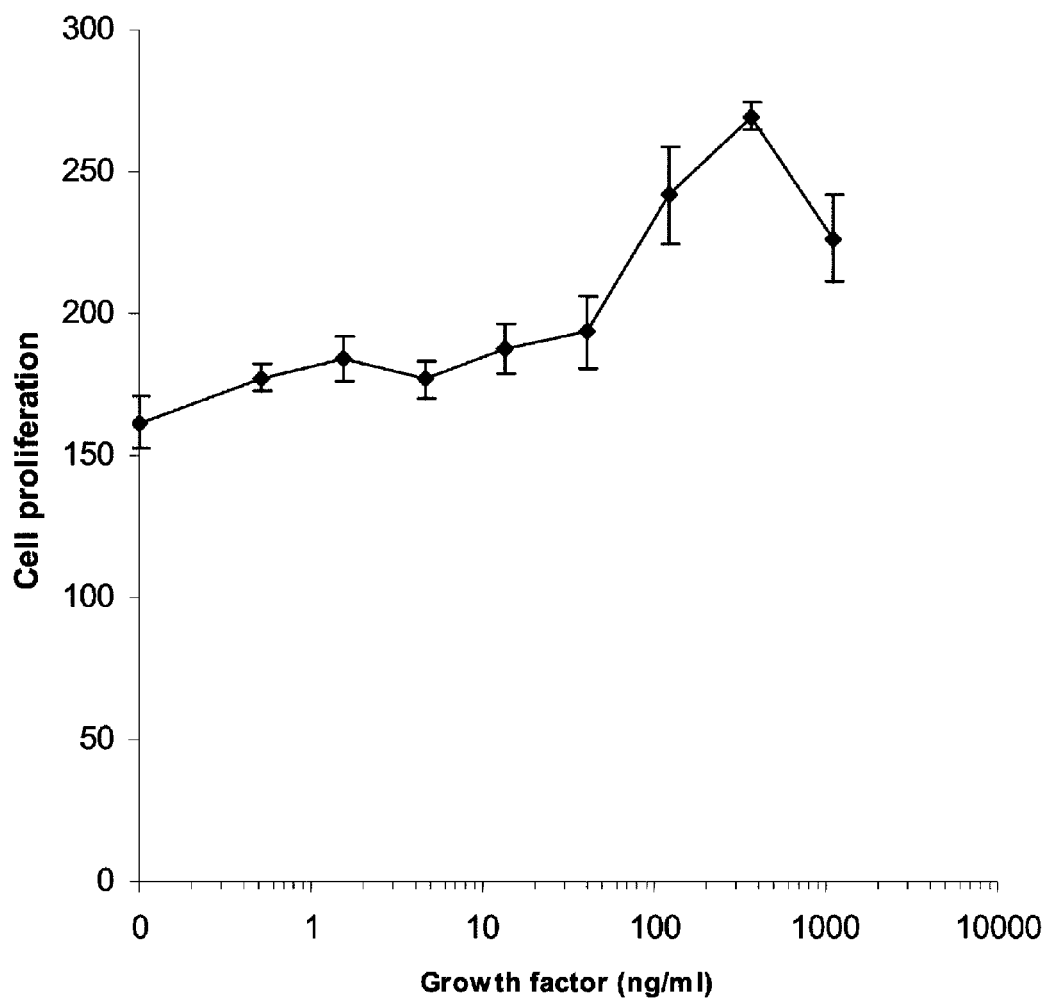
FIG. 7 illustrates the effect of analog PBA2-1 on cell proliferation according to one embodiment of the present invention according to one embodiment of the present invention.

Cell proliferation. The effect of PBA2-1C on cell proliferation was determined with C2C12 cells. The cells were seeded at 2000 cells per well of a 96-well plate and allowed to attach. The medium was changed to one containing low serum and 10 ng/ml of heparin then PBA2-1 was added. After incubation for 3 days, cell numbers was determined by CyQUANT® Cell Proliferation Assay Kit (C-7026) from Molecular Probes. FIG. 7 illustrates the effect of peptide PBA2-1 on cell proliferation. Data is reported as the average±SD.

Example 7

A peptide of the following general structure is synthesized:

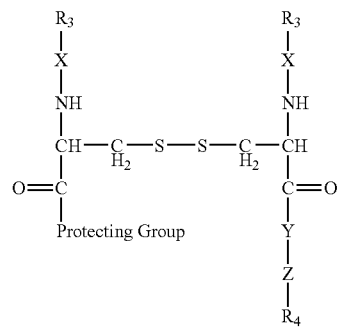

Any suitable carboxy protecting group is employed, if desired, on the second cysteine employed forming a disulfide bridge with the cysteine at the $R_1$ position. Synthesis may proceed without a protecting group, but for most synthetic methods it is desirable to employ a protecting group. The protecting group may be removed following synthesis, or alternatively may be left in place. In one embodiment, an ester is employed as a C-terminal protecting group, such as methyl, ethyl, benzyl or substituted benzyl esters. Other esters may be employed, including allyl esters or t-butyl esters.

Example 8

A mimetic of SDF-1, the peptide designated SD1-1, was synthesized following standard Fmoc protocols using a NovaSyn TGR resin (EMD BioSciences, La Jolla, Calif.). Fmoc-amino acids including aminohexanoic acid (Ahx) were obtained from Peptides International, Inc. (Lexington, Ky.). SD1-1 has the following sequence:

KPVSLSYRAPARFFESHVAK(KPVSLSYRAPARFFESHVA)HxHxHxRK

RKLERIAR-amide.

SDF-1 was purified by RP-HPLC on a C18 column, using a linear gradient 0-60% acetonitrile/water (0.1% trifluoroacetic acid) run over 60 min at 1 ml/min flow rate (detection at 214 nm). The purified peptide generated a single uniform peak on analysis by RP-HPLC as indicated in FIG. 1.

Figure 2:
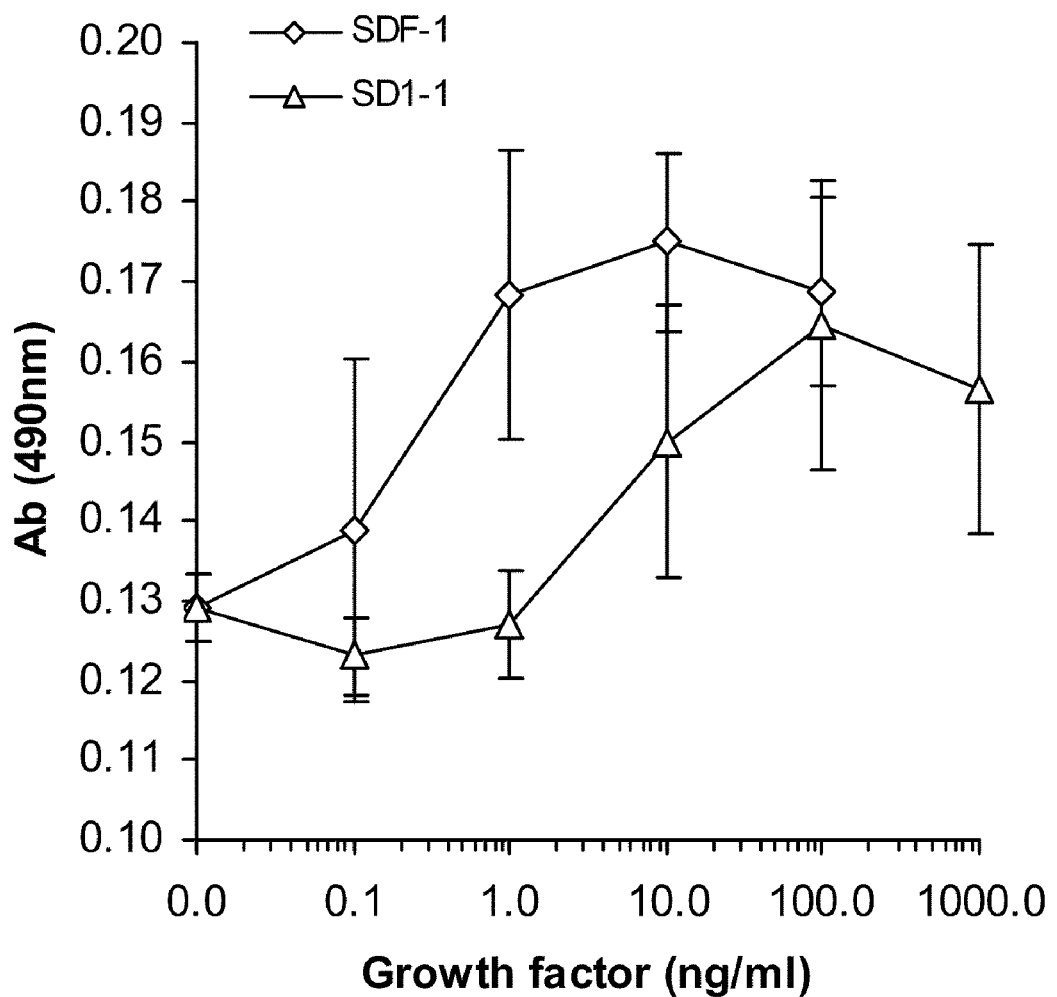
FIG. 2 illustrates a graph of SDF-1 and SD1-1 analog concentration dependent induction of cell proliferation according to one embodiment of the present invention.

Cell proliferation. Sup-T1 cells were obtained from the American Type Culture Collection (Manassas, Va.) and were grown in culture. To monitor the effect of SD1-1 on cell proliferation, Sup-T1 cells were seeded at 100,000 cells per well of a 96-well plate and allowed to attach. The medium was changed to one containing low serum plus SD1-1 and the cells incubated for 3 days after which time the relative cell number was determined using a commercially available kit Referring now to FIG. 2, data in the graph below is reported as the average±SD. Commercially-available recombinant human SDF-1 (diamond) was used as a reference and positive control for comparison of proliferation stimulated by SDF-1 (triangle).

Figure 3:
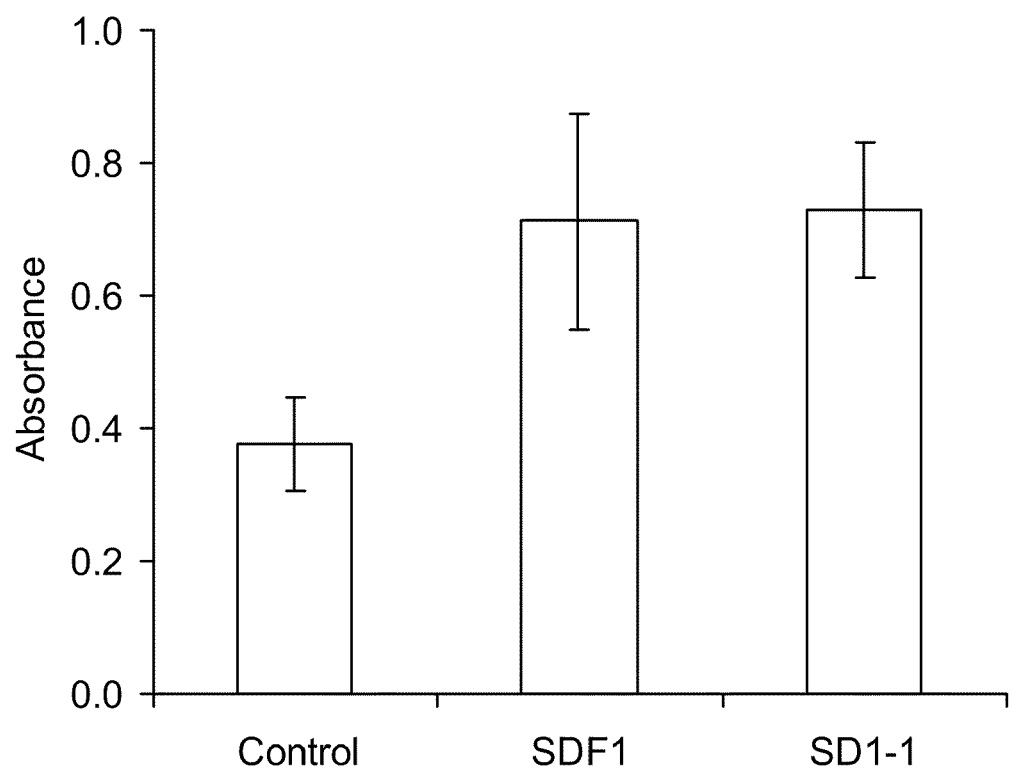
FIG. 3 illustrates a bar graph of SDF-1 and SD1-1 analog induced cell migration according to one embodiment of the present invention.

Cell migration. SD1-1 was evaluated for its ability to induce migration of C2C12 cells using a commercially-available cell migration assay. C2C12 cells were seeded on a trans-well insert containing an 8 μm pore size polycarbonate membrane coated with a thin layer of polymerized collagen. The inserts were placed into wells with medium containing SD1-1. Cells that migrated through the membrane were found on the bottom of the insert membrane. These cells were stained, and the stain extracted and detected on a standard microplate reader (560 nm). Referring now to FIG. 3, the results of cell migration in response to the SD1-1 peptide as compared to SDF-1 peptide or control are illustrated. Data is reported as the average±SD.

Example 9

A mimetic of PDGF, the peptide designated PBA2-1, was synthesized following standard Fmoc protocols using a NovaSyn TGR resin (EMD BioSciences, La Jolla, Calif.). Fmoc-amino acids including aminohexanoic acid (Ahx) were obtained from Peptides International, Inc. (Lexington, Ky.). PBA2-1 has the following sequence:

VRKIEIVRKKK(VRKIEIVRKK)HxHxHxRKRKLERIAR-amide

Figure 4:
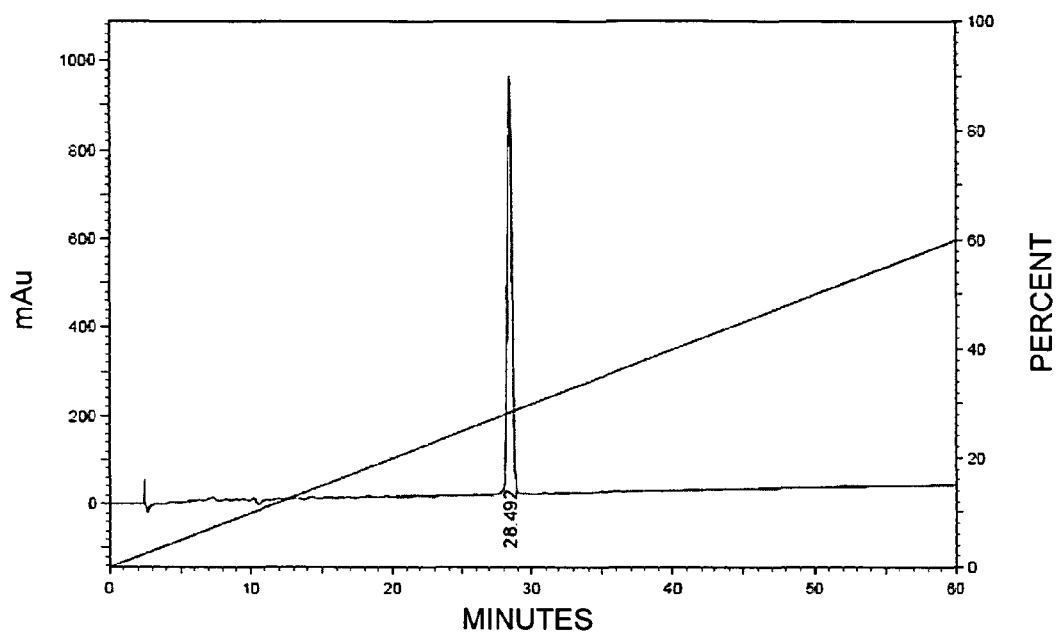
FIG. 4 illustrates a RP-HPLC profile for a PDGF analog according to one embodiment of the present invention according to one embodiment of the present invention.

PBA2-1 was purified by RP-HPLC on a C18 column, using a linear gradient 0-60% acetonitrile/water (0.1% trifluoroacetic acid) run over 60 min at 1 ml/min flow rate (detection at 214 nm). The purified peptide generated a single uniform peak on analysis by RP-HPLC as is illustrated in FIG. 4.

Surface Plasmon Resonance (SPR) Analysis. Real-time biomolecular interactions were analyzed with a BIAcore 2000 system (Biacore Inc., Piscataway, N.J.). Soluble PDGF receptor, recombinant chimera of human PDGF-R-alpha and PSGF-R-beta (R &D Systems, Minneapolis, Minn.), was immobilized on research grade CM5 chips (Biacore Inc., Piscataway, N.J.). Following activation with EDC/NHS, the receptors were immobilized on activated CM5 chips. To obtain kinetic data, different concentrations of analytes in HBS-EP buffer were injected over the sensor chip at a flow rate of 50 μl/min. Peptide binding was measured in resonance units (RU). At the end of each sample injection (120 s) buffer was passed over the sensor surface to monitor the dissociation phase. Reference responses from blank flow cells were subtracted from receptor-containing flow cells for each analyte injection and the kinetic parameters for each interaction were determined by globally fitting the experimental data to a 1:1 interaction with BIAEVALUATION software (Biacore Inc., Piscataway, N.J.). The association rate constant and the dissociation rate constant ($k_a$ and $k_d$, respectively), and the equilibrium dissociation constant ($K_D$) are presented in the Table 4 for the receptors and PBA2-1.

TABLE 4

| Alpha | | | Beta | | |
|---|---|---|---|---|---|
| Ka | Kd | KD | Ka | Kd | KD |
| 4.14E+05 | 9.65E-03 | 2.33E-08 | 3.53E-05 | 7.14E-03 | 2.02E-08 |

Figure 5:
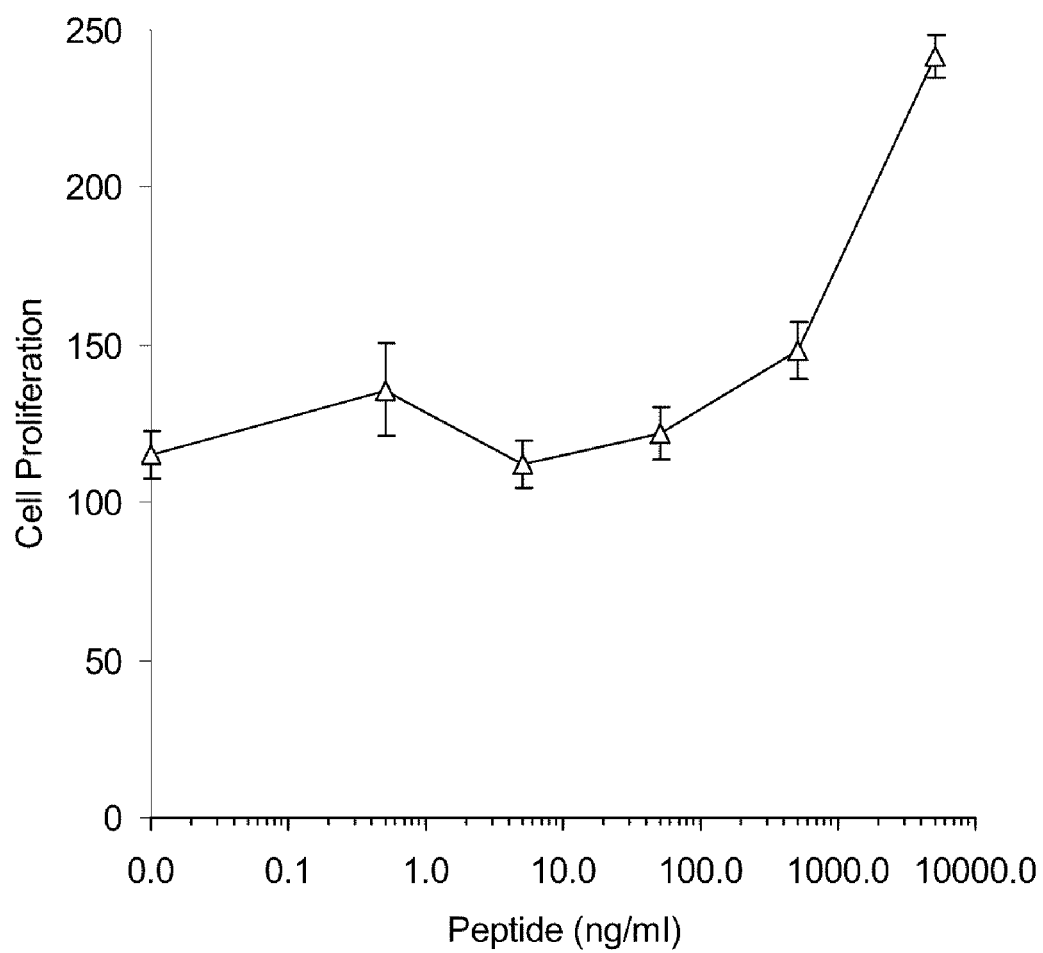
FIG. 5 illustrates results from a cell proliferation assay with PDGF analog PBA2-1 according to one embodiment of the present invention.

Cell proliferation. The effect of PBA2-1 on cell proliferation was determined with C2C12 cells. The cells were seeded at 2000 cells per well of a 96-well plate and allowed to attach. The medium was changed to one containing low serum and 10 ng/ml of heparin then PBA2-1 was added. After incubation for 3 days, cell numbers was determined by CyQUANT® Cell Proliferation Assay Kit (C-7026) from Molecular Probes. FIG. 5 illustrates the effect of peptide PBA2-1 on cell proliferation over a concentration range of PBA2-1 peptide. Data is reported as the average±SD.

The preceding examples can be repeated with similar success by substituting the generically or specifically described peptide sequences, reactants and/or operating conditions of this invention for those used in the preceding examples.

Example 10

A peptide was synthesized based on a sequence of BMP-7. The peptide was designated B7A1-6 and had the sequence:

AISVLYFDDSSNVILKKK(AISVLYFDDSSNVILKK)HxHxHxRKRKLE

RIAR-amide

Figure 8:
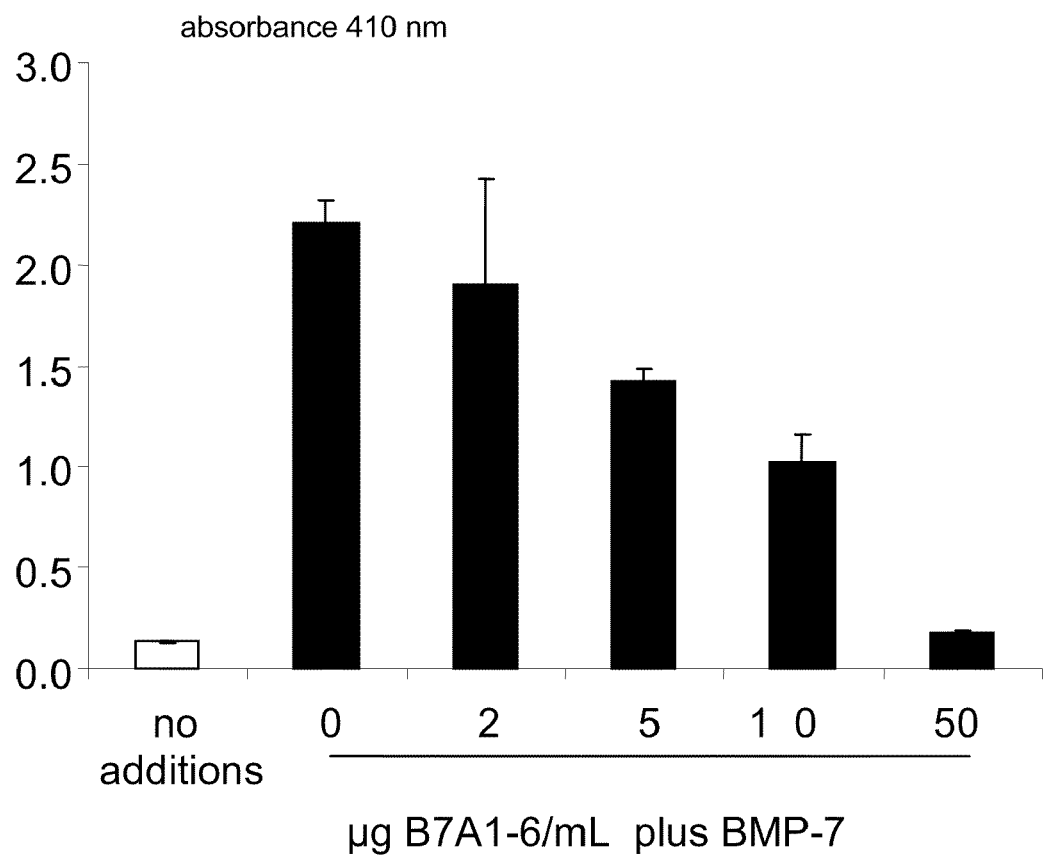
FIG. 8 illustrates a dose-dependant suppression of the activity of BMP-7 by B7A1-6 analog according to one embodiment of the present invention.

This peptide was evaluated using C2C12 cells and in the presence of recombinant BMP-7 and using alkaline phosphatase production as an endpoint. Alkaline phosphatase assays were performed using mouse the pluripotent cell lines C2C12. Cells were plated in 96-well (1×104/well) plates and allowed 24 hours to attach. The medium was then replaced with a serum low medium containing BMP-7 and/or B7A1-6. After several days, cells were rinsed, lysed, and alkaline phosphatase activity measured using p-nitrophenylphosphate as substrate. B7A1-6 had a dose-dependant suppression of the activity of BMP-7 as indicated in FIG. 8.

Example 11

A peptide was synthesized based on a sequence from G-CSF and designated GCSF1. GCSF1 had the sequence:

SFLLKALEQVRKIQYK(SFLLKALEQVRKIQY)HxHxHxRKRKLERIAR-amide

Figure 9:
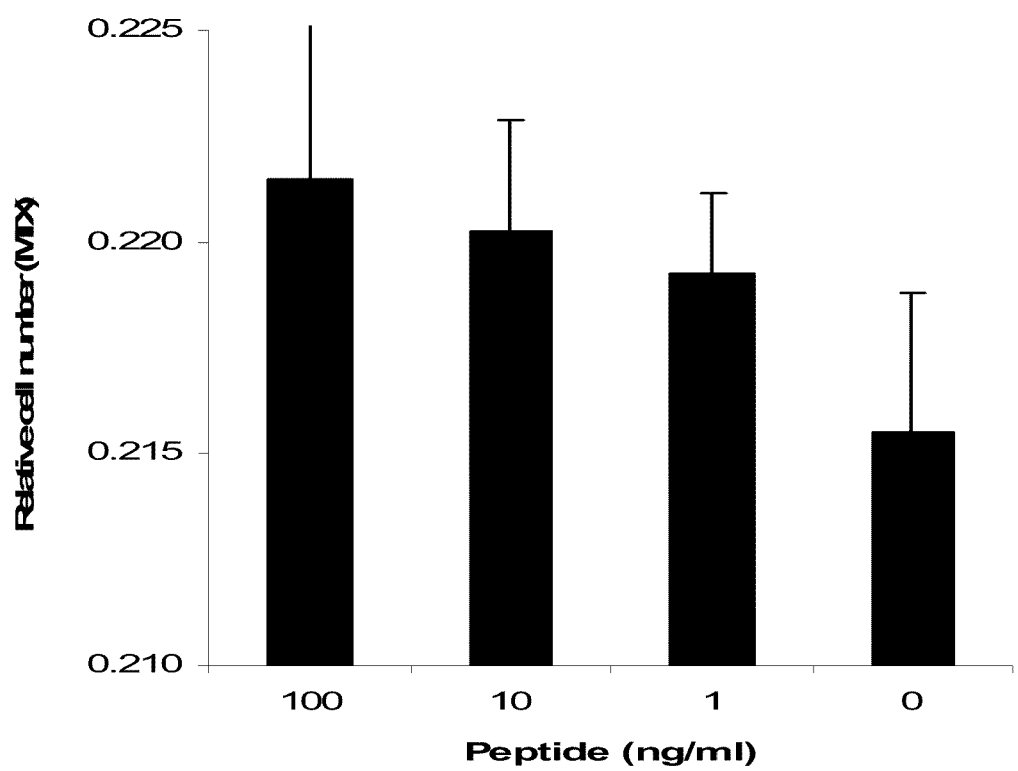
FIG. 9 illustrates augmented cellular growth by GCSF-1 analog according to one embodiment of the present invention.

This peptide was evaluated for augmentation of growth using M-NSF-60 cells in the presence of 0.01 ng rhGCSF. As shown in FIG. 9, the peptide augmented cellular growth as monitored using a commercially-available MTX kit.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

The present invention has been described in terms of preferred embodiments, however, it will be appreciated that various modifications and improvements may be made to the described embodiments without departing from the scope of the invention.

What is claimed is:

1. A heparin-binding growth factor analog of formula I:

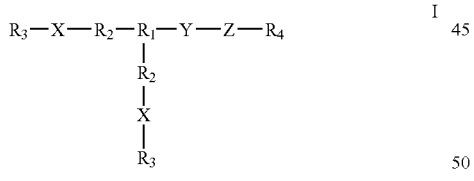

wherein:
Each X consists of SEQ ID NO 107;
$R_1$ is a single trifunctional amino acid residue covalently bonded to each X;
Each $R_2$ is 0 backbone atoms;
Each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative;
$R_4$ is OH such that the terminal group is a carboxyl;
Y consists of Ahx-Ahx-Ahx covalently bonded to $R_1$ and Z; and
Z is selected from the group consisting of SEQ ID NO: 1-6.

2. The heparin-binding growth factor analog of claim 1 wherein X and Z are synthetic peptide chains.

3. A heparin-binding growth factor analog of formula I.

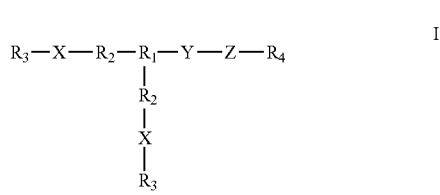

wherein:
$R_1$ is a lysine residue covalently bonded to each X;
Each $R_2$ is 0 backbone atoms;
Each $R_3$ is hydrogen (H) such that the terminal group is $NH_2$, $NH_3^+$, or NH group or a corresponding acylated derivative;
$R_4$ is OH such that the terminal group is a carboxyl;
Each X consists of SEQ ID NO: 107;
Y is Ahx-Ahx-Ahx covalently bonded to $R_1$ and Z; and
Z is SEQ ID NO: 2.

4. The heparin-binding growth factor analog of claim 1 wherein the heparin-binding growth factor analog has an avidity for heparin such that the synthetic heparin-binding growth factor analog binds heparin in 0.15 M NaCl, but is eluted by 1 M NaCl.

5. The heparin-binding growth factor analog of claim 1 wherein $R_1$ is a diamine amino acid.

6. The heparin-binding growth factor analog of claim 1 wherein $R_1$ is an L- or D-diamine amino acid residue selected from the group consisting of 2,3 diamino propionyl amino acid, 2,4 diamino butylic amino acid, lysine and ornithine.

7. The heparin-binding growth factor analog of claim 1 wherein the covalent bonds between $R_1$ and Y comprise an amide, disulfide, thioether, Schiff base, reduced Schiff base, imide, secondary amine, carbonyl, urea, hydrazone or oxime bond.

8. The heparin-binding growth factor analog of claim 1 wherein the covalent bonds between $R_1$ and each X comprise an amide, disulfide, thioether, Schiff base, reduced Schiff base, imide, secondary amine, carbonyl, urea, hydrazone or oxime bond.

9. The heparin-binding growth factor analog of claim 1 wherein the covalent bonds between Y and Z comprise an amide, disulfide, thioether, Schiff base, reduced Schiff base, imide, secondary amine, carbonyl, urea, hydrazone or oxime bond.

10. The heparin-binding growth factor analog of claim 3 is a cyclic peptide with a disulphide bond between each N-terminus cysteine of SEQ ID NO:107 at the X region.

11. A pharmaceutical composition comprising the heparin-binding growth factor analog of any of claim 1, 3 or 10 or a pharmaceutically acceptable salt thereof and a pharmaceutical carrier.

* * * * *